US011572355B2

(12) United States Patent
Bara et al.

(10) Patent No.: US 11,572,355 B2
(45) Date of Patent: Feb. 7, 2023

(54) METHODS FOR SYNTHESIZING VINYLIDENES AND ALKENES

(71) Applicant: The Board of Trustees of The University of Alabama, Tuscaloosa, AL (US)

(72) Inventors: Jason Edward Bara, Tuscaloosa, AL (US); Kathryn Elizabeth O'Harra, Tuscaloosa, AL (US)

(73) Assignee: The Board of Trustees of The University of Alabama, Tuscaloosa, AL (US)

( * ) Notice: Subject to any disclaimer, the term of this patent is extended or adjusted under 35 U.S.C. 154(b) by 0 days.

(21) Appl. No.: 17/322,332

(22) Filed: May 17, 2021

(65) Prior Publication Data
US 2022/0017494 A1    Jan. 20, 2022

Related U.S. Application Data

(60) Provisional application No. 63/052,631, filed on Jul. 16, 2020.

(51) Int. Cl.
C07D 403/06    (2006.01)
(52) U.S. Cl.
CPC .................. *C07D 403/06* (2013.01)
(58) Field of Classification Search
CPC .................................................... C07D 403/06
See application file for complete search history.

(56) References Cited

U.S. PATENT DOCUMENTS

| | | | | |
|---|---|---|---|---|
| 8,377,428 | B2* | 2/2013 | Petersen | A61P 43/00 424/78.1 |
| 2007/0167447 | A1* | 7/2007 | Avolio | C07D 417/06 546/148 |
| 2018/0148521 | A1* | 5/2018 | Ishii | C07C 231/12 |
| 2020/0407211 | A1* | 12/2020 | Schmidt | B67D 7/04 |

FOREIGN PATENT DOCUMENTS

| | | | | |
|---|---|---|---|---|
| JP | 61097309 | A | * | 5/1986 |
| WO | WO-2013089460 | A1 | * | 6/2013 ........... C07D 219/02 |

OTHER PUBLICATIONS

Y. Xiong et al., 79 Journal of Organic Chemistry, 6395-6402 (2014) (Year: 2014).*
Nandeesh et al., 40 New Journal of Chemistry, 2823-2828 (2016) (Year: 2016).*
Hawley's Condensed Chemical Dictionary, p. 1190 (16th ed., 2016, R.J. Larrañaga ed.) (Year: 2016).*
T. Mukaiyama et al., Chemistry Letters, 1041-1044 (1973) (Year: 1973).*
J. McMurry et al., 89 Chemical Reviews, 1513-1524 (1989) (Year: 1989).*
K. Banert et al., 46 Chemical Communications, 4058-4060 (2010) (Year: 2010).*
A. Casimiro-Garcia et al., 42 Journal of Medicinal Chemistry, 4861-4874 (1999) (Year: 1999).*
M. Ogata et al., Tetrahedron Letters, 5011-5014 (1979) (Year: 1979).*
P. Ballesteros et al., 41 Tetrahedron, 5955-5963 (1985) (Year: 1985).*
J. Wang et al., 50 Chemical Communications, 4736-4739 (2014) (Year: 2014).*
Akiyama, T.; Itoh, J.; Yokota, K.; Fuchibe, K., Enantioselective Mannich-Type Reaction Catalyzed by a Chiral Brønsted Acid. Angewandte Chemie International Edition 2004, 43 (12), 1566-1568.
Anderson, E. B.; Long, T. E., Imidazole- and imidazolium-containing polymers for biology and material science applications. Polymer 2010, 51 (12), 2447.
Balasanthiran, V. Chemistry of Bismuth, Chromium and Magnesium Complexes and Their Applications in the Ring-Opening Polymerization of Cyclic Esters and Epoxides. The Ohio State University, 2015. 240 pages.
Ballesteros, P.; Elguero, J.; Claramunt, R. M., Reactivity of azoles towards benzaldehyde and its dimethylacetal. Synthesis of N,N'-diazolylphenylmethanes. Tetrahedron 1985, 41 (24), 5955-5963.
Critchley, J. P., A review of the poly(azoles). Progress in Polymer Science 1970, 2, 47-161.
Crivello, J. V.; Malik, R.; Lai, Y. L., Ketene acetal monomers: Synthesis and characterization. Journal of Polymer Science Part A: Polymer Chemistry 1996, 34 (15), 3091-3102.
Dove, A. P., Organic Catalysis for Ring-Opening Polymerization. ACS Macro Letters 2012, 1 (12), 1409-1412.
Gobbi, A.; Frenking, G., Y-Conjugated compounds: the equilibrium geometries and electronic structures of guanidine, guanidinium cation, urea, and 1,1-diaminoethylene. Journal of the American Chemical Society 1993, 115 (6), 2362-2372.
González, A. I.; Mó, O.; Yáñez, M.; Léon, E.; Tortajada, J.; Morizur, J. P.; Leito, I.; Maria, P. C.; Gal, J. F., Basicity of Acetamidine. Experimental and Theoretical Study. The Journal of Physical Chemistry 1996, 100 (24), 10490-10496.
Jin, X.; Xiao, M.; Ding, Y.; Zhou, J.; Hu, B., Theoretical Insights on A series of Cyclic Energetic Derivatives. ChemistrySelect 2018, 3 (40), 11160-11166.
Jutz, C.; Amschler, J., Über Amidinium-Salze und Ketenaminale. Chemische Berichte 1963, 96 (8), 2100-2108.
Kamlesh J. Padiya, † Sandip Gavade,‡ Bhavana Kardile, † Manojkumar Tiwari,‡ Swapnil Bajare, † Madhav Mane,‡ Vivek Gaware,‡ Shaji Varghese,‡ Dipak Harel,‡ and Suresh Kurhade, Unprecedented "In Water" Imidazole Carbonylation Paradigm Shift for Preparation of Urea and Carbamate. Organic Letters 2012, 14 (11), 2814-2817.
Kantlehner, W., Product Subclass 17: 1,1-Bis(nitrogen-functionalized) Alk-1-enes: 24.2.17.1 Alk-1-ene-1,1-diamines. Science of Synthesis 2006, 24, 571-705.
Keller, Paul A., and Jody Morgan, Alk-1-ene-1,1-diamines with retention of the functional group. In Science of Synthesis, 2006; vol. 24, pp. 707-746.

(Continued)

*Primary Examiner* — Alexander R Pagano
(74) *Attorney, Agent, or Firm* — Meunier Carlin & Curfman LLC

(57) ABSTRACT

The present disclosure provide synthetic methods for the synthesis of N-substituted vinylidene and alkene compounds in addition to compounds formed from such methods.

20 Claims, 24 Drawing Sheets

(56) References Cited

OTHER PUBLICATIONS

Kishore, V.; Kumar, S.; Parmar, S. S.; Stenberg, V. I., Anti-Inflammatory and Antiproteolytic Properties of 1-(1-Naphthylacetyl)-3-substituted Carbamides. Journal of Pharmaceutical Sciences 1976, 65 (7), 1078-1081.

Kizhnyaev, V. N.; Krakhotkina, E. A.; Petrova, T. L.; Kazantseva, M. V.; Pokatilov, F. A.; Verkhozina, O. N., Synthesis and properties of azole-containing ionenes. Polymer Science Series B 2011, 53 (3-4), 144-150.

Kleinpeter, E.; Schulenburg, A., Quantification of the push-pull effect in substituted alkenes. Tetrahedron Letters 2005, 46 (36), 5995-5997.

McElvain, S. M., and Bryce E. Tate. "Nitrogen Analogs of the Ketene Acetals." Journal of the American Chemical Society 67.2 (1945): 202-204.

McElvain, S. M., The Ketene Acetals. 1949. McElvain, S. M. "The Ketene Acetals." Chemical Reviews 45.3 (1949): 453-492.

Mote, S. P.; Deshmukh, S. P., Synthesis and Anti-Microbial Activity Of Novel Acetylated Maltosyl Carbamides, Benzothiazolyl Carbamides And Carbamates. Rasayan Journal of Chemistry 2011, 4 (1), 29-35.

Naumann, S., Synthesis, properties & applications of N-heterocyclic olefins in catalysis. Chemical Communications 2019, 55 (78), 11658-11670.

Neidlein, R.; Klotz, U. J., Synthesen, spektroskopische Eigenschaften von Alkylmercaptoalkylaminomethylensulfonamiden und chemisches Reaktionsverhalten von 1,1-Bis-(dimethylamino)-ethylen. Monatshefte für Chemie /Chemical Monthly 1985, 116 (5), 651-660.

Nugent, J.; Campbell, S. G.; Vo, Y.; Schwartz, B. D., Solvent-Free Synthesis of Cyanoformamides from Carbamoyl Imidazoles. European Journal of Organic Chemistry 2017, 2017 (34), 5110-5118.

Ogata, M.; Matsumoto, H.; Kida, S.; Shimizu, S., Reaction of N,N'-carbonyldiimidazole and N,N'-thionyldiimidazole with carbonyl compounds: a new imidazole transfer reaction. Tetrahedron Letters 1979, 20 (52), 5011-5014.

O'Harra, K. E.; Bara, J. E., Toward controlled functional sequencing and hierarchical structuring in imidazolium ionenes. Polymer International 2020.

Palaniraja, J.; Roopan, S. M., UV-light induced domino type reactions: synthesis and photophysical properties of unreported nitrogen ring junction quinazolines. RSC Advances 2015, 5 (47), 37415-37423.

Parmar, S. S.; Dwivedi, C.; Ali, B., Substituted carbamides: Interrelationship between anticonvulsant activity and inhibition of nicotinamide adenine dinucleotide-dependent pyruvic acid oxidation. Journal of Pharmaceutical Sciences 1972, 61 (9), 1366-1369.

Paul, R.; Anderson, G. W., N,N'-Carbonyldiimidazole, a New Peptide Forming Reagent1. Journal of the American Chemical Society 1960, 82 (17), 4596-4600.

Ogasawara, M., Product class 1: cumulenes. In Science of Synthesis, 2007; vol. 44, pp. 9-70.

Zwanenburg, B., Product class 3: thioaldehyde and thioketone S,S-dioxides and oxyimides (sulfenes and derivatives). In Science of Synthesis, 2004; vol. 27, pp. 123-134.

Rickborn, B., The Retro-Diels-Alder Reaction Part II. Dienophiles with One or More Heteroatom. Organic Reactions 2004, 223-287; 608-642.

Roberto Di Santo; Tafi, A.; Costi, R.; Botta, M.; Artico, M.; Corelli, F.; Forte, M.; Caporuscio, F.; Angiolella, L.; Palamara, A. T., Antifungal Agents. 11. N-Substituted Derivatives of 1-[(Aryl)(4-aryl-1H-pyrrol-3-yl)methyl]-1H-imidazole: Synthesis, Anti-Candida Activity, and QSAR Studies. Journal of Medicinal Chemistry 2005, 48, 5140-5153.

Roy, M. M. D.; Rivard, E., Pushing Chemical Boundaries with N-Heterocyclic Olefins (NHOs): From Catalysis to Main Group Element Chemistry. Accounts of Chemical Research 2017, 50 (8), 2017-2025.

Shevlin, P. B.; McPherson, D. W.; Melius, P., Reaction of atomic carbon with ammonia. The mechanism of formation of amino acid precursors. Journal of the American Chemical Society 1983, 105 (3), 488-491.

Sogah, D. Y.; Hertler, W. R.; Webster, O. W.; Cohen, G. M., Group transfer polymerization—polymerization of acrylic monomers. Macromolecules 1987, 20 (7), 1473-1488.

Staudinger, H.; Rathsam, G., Ketene: Über Ketenacetale. XL. Mitteilung. Helvetica Chimica Acta 1922, 5 (5), 645-655. In German.

Sung, K.; Wu, S.-H.; Wu, R.-R.; Sun, S.-Y., NMR and ab Initio Studies of Amination of Ketenimine: Direct Evidence for a Mechanism Involving a Vinylidenediamine as an Intermediate. The Journal of Organic Chemistry 2002, 67 (12), 4298-4303.

Taylor, J. E.; Bull, S. D.; Williams, J. M. J., Amidines, isothioureas, and guanidines as nucleophilic catalysts. Chemical Society Reviews 2012, 41 (6), 2109-2121.

Trost, B. M.; McClory, A., Metal Vinylidenes as Catalytic Species in Organic Reactions. Chemistry—An Asian Journal 2008, 3 (2), 164-194.

Von Angerer, S., Product class 12: pyrimidines. In Science of Synthesis, 2011; vol. 16, pp. 103-491.

Weingarten, H.; Wager, J. S., The oxidative coupling reaction of vinylidenebisdialkylamines. Tetrahedron Letters 1969, 10 (38), 3267-3268.

Wenzel, A. G.; Jacobsen, E. N., Asymmetric Catalytic Mannich Reactions Catalyzed by Urea Derivatives: Enantioselective Synthesis of β-Aryl-β-Amino Acids. Journal of the American Chemical Society 2002, 124 (44), 12964-12965.

Xiong, Y.; Zhang, X.; Huang, T.; Cao, S., Synthesis of N-(alpha-fluorovinyl)azoles by the reaction of difluoroalkenes with azoles. J Org Chem 2014, 79 (14), 6395-402.

Yamaguchi, K.; Yabushita, S.; Fueno, T., Zwitterionic mechanisms for photooxygenation reactions of n-activated c-c double bonds: full geometry optimizations of the diradical and zwitterionic intermediates by ab initio SCF method. Chemical Physics Letters 1981, 78 (3), 566-571.

Zhang, C.; Shi, Y.-L.; Zhang, L.-Y.; Yuan, D.-P.; Ban, M.-T.; Zheng, J.-Y.; Liu, D.-H.; Guo, S.-N.; Cui, D.-M., NaOH-promoted reaction of 1,1-dihaloalkenes and 1H-azoles: synthesis of dihetaryl substituted alkenes. New Journal of Chemistry 2018, 42 (21), 17732-17739.

* cited by examiner

METHODS FOR SYNTHESIZING VINYLIDENES AND ALKENES

CROSS-REFERENCE TO RELATED APPLICATIONS

This application claims the benefit of priority to U.S. Provisional Patent Application No. 63/052,631, filed Jul. 16, 2021, the disclosure of which is incorporated herein by reference in its entirety.

STATEMENT REGARDING FEDERALLY SPONSORED RESEARCH OR DEVELOPMENT

This invention was made with government support under Grant No. DE-SC0018181 awarded by the Department of Energy. The Government has certain rights in the invention.

TECHNICAL FIELD

This disclosure relates to synthetic methods, and more particularly to methods for preparing nitrogen-substituted vinylidene and alkene compounds.

BACKGROUND

Compounds containing vinylidene and alkene functional groups find many applications such as in the development of pharmaceuticals or in polymer manufacture. For example, vinylidene chloride or fluoride are monomer precursors for the widely used plastics polyvinylidene chloride and fluoride, respectively. Due to their wide applicability in the manufacture of various products, there is a clear need for simple and reliable methods for the synthesis of vinylidene-containing compounds.

SUMMARY

The present disclosure provides methods for the synthesis of N-substituted vinylidene compounds from carbonyl-containing compounds using a simple, one-step process. The synthesized N-substituted vinylidene compounds may then be used in the synthesis of novel materials, for example ionic liquids or polymers.

The details of one or more embodiments of the disclosure are set forth in the description below. Other features, objects, and advantages of the disclosure will be apparent from the description and from the claims.

DESCRIPTION OF DRAWINGS

Like reference symbols in the various drawings indicate like elements.

DETAILED DESCRIPTION

Figure 1:
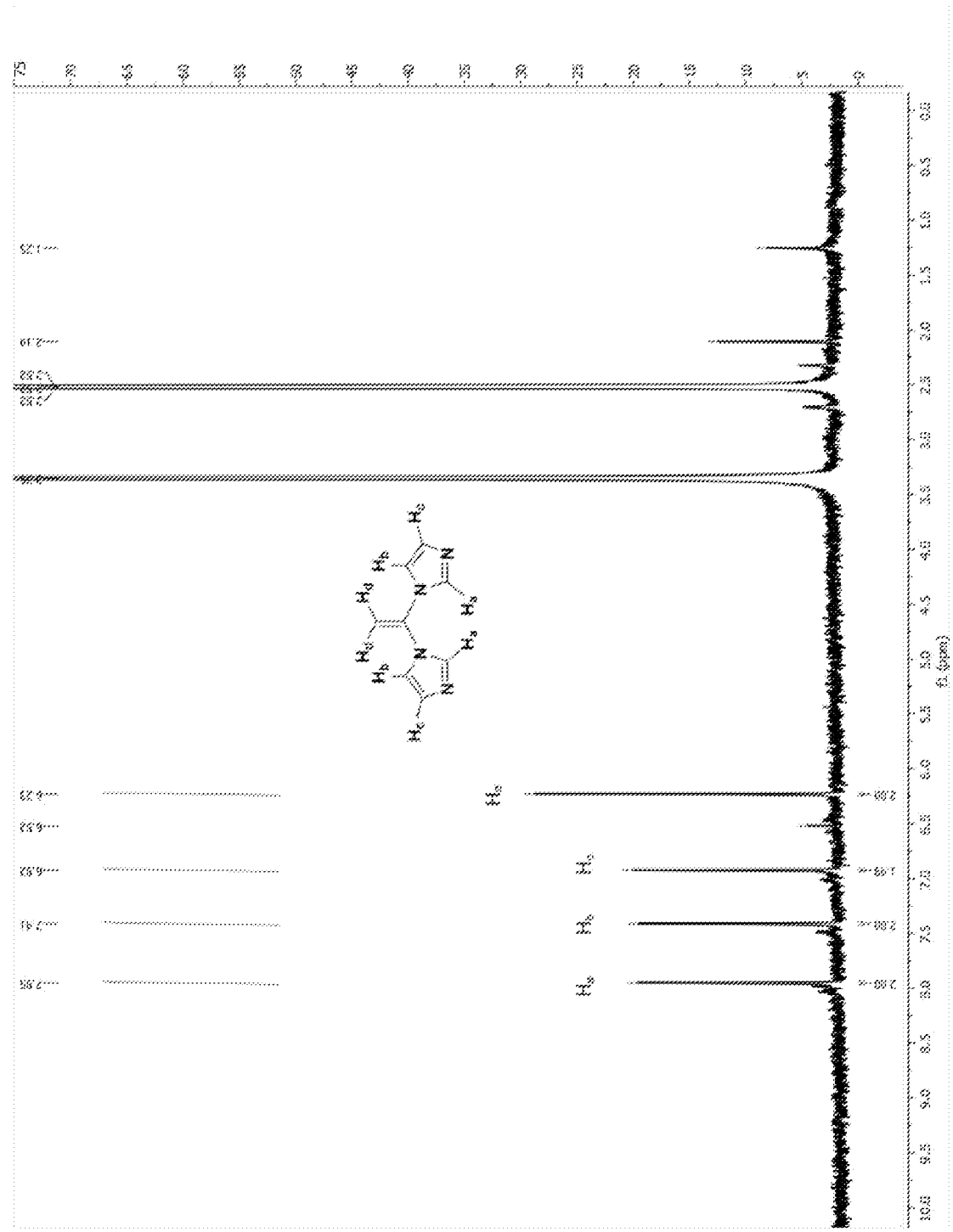
FIG. 1 is a final $^1$H-NMR (500 MHz, $d_6$-DMSO) of 1,1'-(ethene-1,1-diyl)bis(1H-imidazole) product formed from 1,1'-carbonyldi(imidazole) with 4 eq. paraformaldehyde.

Many modifications and other embodiments disclosed herein will come to mind to one skilled in the art to which the disclosed compounds, compositions and methods pertain having the benefit of the teaching presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of the disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from and combined with the features of any of the other several embodiments without departing from the scope and spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or description that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuations, or the number or type of aspects described in the specification.

All publications mentioned herein are incorporated herein by reference to disclose and described the methods and/or materials in connection with which the publications are cited. The publications discussed herein are provided solely for the disclosure prior to the filing date of the present application. The dates of publication provided herein can be different from the actual publication dates, which can require independent confirmation.

It is also to be understood that the terminology used herein is for the purpose of describing particular aspects only and is not intended to be limited. Unless defined otherwise, all technical and scientific terms used herein have the same meaning as commonly understood by one of ordinary skill in the art to which the disclosed compounds, compositions, and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated feature, integers, steps, or components as referred to, but does not preclude the presence or addition of one or more features, integers, steps, or components, or groups thereof. Moreover, each of the terms "by", "comprising", "comprises", "comprised of", "including", "includes", "included", "involving", "involves", "involved", and "such as" are used in their open, non-limiting sense and may be used interchangeably. Further, the term "comprising" is intended to include examples and aspects encompassed by the terms "consisting essentially of" and "consisting of". Similarly, the term "consisting essentially of" is intended to include examples encompassed by the term "consisting of".

As used in the specification and the appended claims, the singular forms "a", "an" and "the" include plural referents unless the context clearly dictates otherwise. Thus, for example, reference to "a compound" includes, but is not limited to, two or more such compounds, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about", it will be understood that the particular value forms a further aspect. For example, if the value "about 10" is disclosed, then "10" is also disclosed.

As used herein, the terms "about", "approximate", "at or about", and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably be determined. In such cases, it is generally understood, as used herein, that "about" and "at or about" mean the nominal value indicated ±10% variation unless otherwise indicated or inferred. In general, an amount, size, formulation, parameter, or other quantity or characteristic is "about", "approximate", or "at or about" whether or not expressly stated to be such. It is understood that where "about", "approximate", or "at or about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not.

Chemical Definitions

Compounds are described using standard nomenclature. Unless defined otherwise, all technical and scientific terms used herein have the same meaning as is commonly understood by one of skill in the art to which this invention belongs.

The compounds described herein include enantiomers, mixtures of enantiomers, diastereomers, tautomers, racemates and other isomers, such as rotamers, as if each is specifically described, unless otherwise indicated or otherwise excluded by context. In particular, any compound containing an alkene group is inclusive of both the Z and E isomers of the alkene, either alone or as a combination in a mixture, irrespective of the particular configuration shown.

A dash ("-") that is not between two letters or symbols is used to indicate a point of attachment for a substituent. For example, —(C=O)NH$_2$ is attached through the carbon of the keto (C=O) group.

The term "substituted", as used herein, means that any one or more hydrogens on the designated atom or group is replaced with a moiety selected from the indicated group, provided that the designated atom's normal valence is not exceeded and the resulting compound is stable. For example, when the substituent is oxo (i.e., =O) then two hydrogens on the atom are replaced. For example, a pyridyl group substituted by oxo is a pyridine. Combinations of substituents and/or variables are permissible only if such combinations result in stable compounds or useful synthetic intermediates. A stable active compound refers to a compound that can be isolated and can be formulated into a dosage form with a shelf life of at least one month. A stable manufacturing intermediate or precursor to an active compound is stable if it does not degrade within the period needed for reaction or other use. A stable moiety or substituent group is one that does not degrade, react or fall apart within the period necessary for use. Non-limiting examples of unstable moieties are those that combine heteroatoms in an unstable arrangement, as typically known and identifiable to those of skill in the art.

Any suitable group may be present on a "substituted" or "optionally substituted" position that forms a stable molecule and meets the desired purpose of the invention and includes, but is not limited to: alkyl, haloalkyl, alkoxy, alkenyl, alkynyl, aryl, heteroaryl, cycloalkyl, heterocycle, aldehyde, amino, carboxylic acid, ester, ether, halo, hydroxy, keto, nitro, cyano, azido, silyl, sulfo-oxo, sulfonyl, sulfone, sulfoxide, sulfonylamino, or thiol.

"Alkyl" is a straight chain or branched saturated aliphatic hydrocarbon group. In certain embodiments, the alkyl is $C_1$-$C_2$, $C_1$-$C_3$, or $C_1$-$C_6$ (i.e., the alkyl chain can be 1, 2, 3, 4, 5, or 6 carbons in length). The specified ranges as used herein indicate an alkyl group with length of each member of the range described as an independent species. For example, $C_1$-$C_6$alkyl as used herein indicates an alkyl group having from 1, 2, 3, 4, 5, or 6 carbon atoms and is intended to mean that each of these is described as an independent species and $C_1$-$C_4$alkyl as used herein indicates an alkyl group having from 1, 2, 3, or 4 carbon atoms and is intended to mean that each of these is described as an independent species. When $C_0$-$C_n$alkyl is used herein in conjunction with another group, for example ($C_3$-$C_7$cycloalkyl)$C_0$-$C_4$alkyl, or —$C_0$-$C_4$($C_3$-$C_7$cycloalkyl), the indicated group, in this case cycloalkyl, is either directly bound by a single covalent bond ($C_0$alkyl), or attached by an alkyl chain, in this case 1, 2, 3, or 4 carbon atoms. Alkyls can also be attached via other groups such as heteroatoms, as in —O—$C_0$-$C_4$alkyl($C_3$-$C_7$cycloalkyl). Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane. In one embodiments, the alkyl group is optionally substituted as described herein.

"Cycloalkyl" is a saturated mono- or multi-cyclic hydrocarbon ring system. When composed of two or more rings, the rings may be joined together in a fused or bridged fashion. Non-limiting examples of typical cycloalkyl groups include cyclopropyl, cyclobutyl, cyclopentyl, cyclohexyl, and cycloheptyl. In one embodiment, the cycloalkyl group is optionally substituted as described herein.

"Alkenyl" is a straight or branched chain aliphatic hydrocarbon group having one or more carbon-carbon double bonds, each of which is independently either cis or trans, that may occur at a stable point along the chain. Non-limiting examples include $C_2$-$C_4$alkenyl and $C_2$-$C_6$alkenyl (i.e., having 2, 3, 4, 5, or 6 carbons). The specified ranges as used herein indicate an alkenyl group having each member of the range described as an independent species, as described above for the alkyl moiety. Examples of alkenyl include, but are not limited to, ethenyl and propenyl. In one embodiment, the alkenyl group is optionally substituted as described herein.

"Alkynyl" is a straight or branched chain aliphatic hydrocarbon group having one or more carbon-carbon triple bonds that may occur at any stable point along the chain, for example, $C_2$-$C_4$alkynyl or $C_2$-$C_6$alkynyl (i.e., having 2, 3, 4, 5, or 6 carbons). The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl. In one embodiment, the alkynyl group is optionally substituted as described herein.

"Alkoxy" is an alkyl group as defined above covalently bound through an oxygen bridge (—O—). Examples of alkoxy include, but are not limited to, methoxy, ethoy, n-propoxy, isopropoxy, n-butoxy, 2-butoxy, tert-butoxy, n-pentoxy, 2-pentoxy, 3-pentoxy, isopentoxy, neopentoxy, n-hexoxy, 2-hexoxy, 3-hexoxy, and 3-methylpentoxy. Similarly, an "alkylthio" or "thioalkyl" group is an alkyl group as defined above with the indicated number of carbon atoms covalently bound through a sulfur bridge (—S—). In one embodiment, the alkoxy group is optionally substituted as described herein.

"Alkanoyl" is an alkyl group as defined above covalently bound through a carbonyl (C=O) bridge. The carbonyl carbon is included in the number of carbons, for example $C_2$alkanoyl is a $CH_3(C=O)$— group. In one embodiment, the alkanoyl group is optionally substituted as described herein.

"Haloalkoxy" indicates a haloalkyl group as defined herein attached through an oxygen bridge (oxygen of an alcohol radical).

"Halo" or "halogen" indicates, independently, any of fluoro, chloro, bromo or iodo.

"Aryl" indicates an aromatic group containing only carbon in the aromatic ring or rings. In one embodiment, the aryl group contains 1 to 3 separate or fused rings and is 6 to 14 or 18 ring atoms, without heteroatoms as ring members. When indicated, such aryl groups may be further substituted with carbon or non-carbon atoms or groups. Such substitution may include fusion to a 4- to 7- or 5- to 7-membered saturated or partially unsaturated cyclic group that optionally contains 1, 2, or 3 heteroatoms independently selected from N, O, B, P, Si and S, to form, for example, a 3,4-methylenedioxyphenyl group. Aryl groups include, for example, phenyl and naphthyl, including 1-naphthyl and 2-naphthyl. In one embodiment, aryl groups are pendant. An example of a pendant ring is a phenyl group substituted with a phenyl group. In one embodiment, the aryl group is optionally substituted as described herein.

The term "heterocycle" refers to saturated and partially saturated heteroatom-containing ring radicals, where the heteroatoms may be selected from N, O, and S. The term heterocycle includes monocyclic 3-12 members rings, as well as bicyclic 5-16 membered ring systems (which can include fused, bridged, or spiro bicyclic ring systems). It does not include rings containing —O—O—, —O—S—, and —S—S— portions. Examples of saturated heterocycle groups including saturated 4- to 7-membered monocyclic groups containing 1 to 4 nitrogen atoms [e.g., pyrrolidinyl, imidazolidinyl, piperidinyl, pyrrolinyl, azetidinyl, piperazinyl, and pyrazolidinyl]; saturated 4- to 6-membered monocyclic groups containing 1 to 2 oxygen atoms and 1 to 3 nitrogen atoms [e.g., morpholinyl]; and saturated 3- to 6-membered heteromonocyclic groups containing 1 to 2 sulfur atoms and 1 to 3 nitrogen atoms [e.g., thiazolidinyl]. Examples of partially saturated heterocycle radicals include, but are not limited, dihydrothienyl, dihydropyranyl, dihydrofuryl, and dihydrothiazolyl. Examples of partially saturated and saturated heterocycle groups include, but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydroquinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3,-dihydro-1H-benzo[d]isothazol-6-yl, dihydropyranyl, dihydrofuryl, and dihydrothiazolyl. Bicyclic heterocycle includes groups wherein the heterocyclic radical is fused with an aryl radical wherein the point of attachment is the heterocycle ring. Bicyclic heterocycle also includes heterocyclic radicals that are fused with a carbocyclic radical. Representative examples include, but are not limited to, partially unsaturated condensed heterocyclic groups containing 1 to 5 nitrogen atoms, for example indoline and isoindoline, partially unsaturated condensed heterocyclic groups containing 1 to 2 oxygen atoms and 1 to 3 nitrogen atoms, partially unsaturated condensed heterocyclic groups containing 1 to 2 sulfur atoms and 1 to 3 nitrogen atoms, and saturated condensed heterocyclic groups containing 1 to 2 oxygen or sulfur atoms.

"Heteroaryl" refers to a stable monocyclic, bicyclic, or multicyclic aromatic ring which contains from 1 to 3, or in some embodiments 1, 2, or 3 heteroatoms selected from N, O, S, B, and P (and typically selected from N, O, and S) with remaining ring atoms being carbon, or a stable bicyclic or tricyclic system containing at least one 5, 6, or 7 membered aromatic ring which contains from 1 to 3, or in some embodiments from 1 to 2, heteroatoms selected from N, O, S, B, or P, with remaining ring atoms being carbon. In one embodiments, the only heteroatom is nitrogen. In one embodiment, the only heteroatom is oxygen. In one embodiment, the only heteroatom is sulfur. Monocyclic heteroaryl groups typically have from 5 to 6 ring atoms. In some embodiments, bicyclic heteroaryl groups are 8- to 10-membered heteroaryl groups, that is groups containing 8 or 10 ring atoms in which one 5-, 6-, or 7-membered aromatic ring is fused to a second aromatic or non-aromatic ring, wherein the point of attachment is the aromatic ring. When the total number of S and O atoms in the heteroaryl group excess 1, these heteroatoms are not adjacent to one another. In one embodiment, the total number of S and O atoms in the heteroaryl group is not more than 2. In another embodiment, the total number of S and O atoms in the heteroaryl group is not more than 1. Examples of heteroaryl groups include, but are not limited to, pyridinyl, imidazolyl, imidazopyridinyl, pyrimidinyl, pyrazolyl, triazolyl, pyrazinyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

Vinylidene compounds are those which incorporate the functional group $R^aR^bC=CH_2$, where the connectivity of the central carbon to $R^a$ and $R^b$ can be through carbon atoms or heteroatoms. The most well-known vinylidene compounds are vinylidene chloride ($Cl_2C=CH_2$) and vinylidene fluoride ($F_2C=CH_2$), which are the respective parent monomers of polyvinylidene chloride (PVDC) and polyvinylidene fluoride (PVDF). Vinylidene compounds where $R^a$ and $R^b$ are connected through carbons are rare with the exception of isobutylene (($CH_3)_2C=CH_2$), a key intermediate for a variety of organic compounds including methyl tert-butyl ether (MTBE) and poly(isobutylene) ("butyl rubber"). Other small hydrocarbon vinylidene molecules are known, including 2-methyl-1-butene and 1,1-diphenylethylene. Vinylidene compounds where at least one substituent group is connected to the central carbon through either at least one oxygen and/or nitrogen atom have limited examples (e.g., 2-methoxypropene, 2-(dimethylamino)propene, 1,1-dimethoxyethene, and 1-(dimethylamino)-1-methoxyethene). More commonly, greater substitution is present in such molecules, therefore making them not fit within the strict definition of a vinylidene. Those connected through two oxygen atoms are called "ketene acetals", which have been known since the 1920s (1) and find use as intermediates in a multitude of organic reactions, including the preparation of alpha-amino acids and controlled polymerizations (2-6). Analogous species where the central carbon atom is connected through two nitrogen atoms are known as ketene aminals (7,8). It is known that the adjacent electronegative atoms (either nitrogen or oxygen) in these ketene molecules influence the behavior and activate the methylene carbon of the alkenyl segment.

However, such molecules could prove to be incredibly valuable for a variety of uses, especially in pharmaceuticals, catalysis, and energetic applications. While 1,1-diaminoethene (DAE) and similar compounds exist in the literature, the work is primarily theoretical/computational studies focused on electronic structure calculations and energetics (9-16). The only experimental reactions that have been demonstrated and with DAE and α,β-unsaturated carbonyl derivatives, which cyclize to form pyrimidines or other N-containing ring systems (17, 18). Pyrimidines naturally occur in several nucleotides and are used in synthetic barbiturates and HIV drugs. N,N,N',N'-tetramethylethene-1,1-diamine (TMDA) has been utilized in cumulene (—C=C=C—) synthesis from coupling with 1,1'-dihaloalkane (19). TMDA has also been used to modify unsaturated ring systems via cycloaddition (20, 21). TMDA in the presence of a sulfonyl halide group forms substituted thiete-dioxide rings (22). TMDA and bis-alkylmercaptomethyleneimides were shown to form isothioureas and 1-aza-butadiene derivatives (23). Diaminoalkenes and thioureas have been explored as nucleophilic catalysts for reactions including ring-opening polymerizations of lactones, epoxies, and isocyanates (24, 25). Diaminoalkenes are most commonly found within the substructures of ligands and complexes (26). Amidines, an isomer of diaminoalkenes, have also exhibited catalytic activity in a variety of reactions (27). Generally, metal vinylidenes have also been shown to catalyze various organic reactions (28). N-vinyl azole derivatives have been reported, from the reaction of azoles with 1,1-dihaloalkenes (29,30). N-heterocyclic olefins bear structural similarity to these aforementioned compounds, wherein the N-atoms connected to the C═C segment are within a heterocycle, and have also been demonstrated as diverse catalysts (31, 32).

Despite these fundamental studies of the nitrogen-analogs of ketene acetals (i.e., ketene aminals) and foundational investigation of simple 1,1'-diaminoethene derivatives, few analogs of this form include complex or cyclic substituents on the nitrogen atoms or are synthetically accessible. In fact, no N-mediated vinylidenes are shown in the literature summarizes 1,1-bis(nitrogen-functionalized) alk-1-enes (25).

1,1'-carbonyldiimidazole (CDI), 1,1'-thiocarbonyldiimidazole (TCDI), and 1,1'-sulfinylbis(1H-imidazole) have all been demonstrated to react with various substrates, serving as imidazole or carbonyl transfer agents (33). Ogata et al. investigated the reaction between aldehydes and ketones with 1,1'-thionyldiimidazole (TDI), which resulted in imidazole transfer and yielded diimidazole and monoimidazole products from several derivatives. While thionyl or thiocarbonyl transfer reactions via TDI or TCDI are well known, only CDI is an inexpensive, common, and versatile substrate with diverse reaction potential, even though the aforementioned work did not observe reactions between CDI and aldehydes or ketones. Since this early work, the continued study of CDI has gravitated toward the synthesis of asymmetric carbamides and carbamates, as one imidazole moiety of CDI can be displaced by alcohols and amines (29, 34, 35). Additionally, the catalyzed reactions of CDI with benzaldehydes, or corresponding benzaldehyde dimethyl acetals, have been shown to produce 1,1'-(phenylmethylene)diimidazole compounds (36). 1,1'-carbonyldiazole compounds are powerful synthetic tools (37) but have not been demonstrated in the synthesis of heterocyclic N,N'vinylidene or HKA compounds.

The present disclosure demonstrates the formation of azole-mediated vinylidene products (e.g., several 1,1'-(ethene-1,1-diyl)diazoles and 1,1'-(prop-1-ene-1,1-diyl)diimidazole), and methods for their synthesis via reaction of symmetric carbamides with at least 3 equivalents of paraformaldehyde (PFA) (or dimethoxymethane or 1,3,5-trioxane) and acetaldehyde, respectively. The principal demonstration of the C═C bond formation is the reaction of CDI with at least 3 equivalents of PFA to form 1,1'-vinylidenediimidazole (VDI). This transformation was expanded and confirmed to apply in other cases under similar reaction conditions, including the reaction of at least 3 equivalents of PFA with 1,1'-carbonyldi(2-methylimidazole) or 1,1'-carbonyldi(1,2,4-triazole) to form the corresponding 1,1'-(ethene-1,1-diyl)bis(2-methyl-1H-imidazole) or 1,1'-(ethene-1,1-diyl)bis(1H-1,2,4-triazole) derivatives, respectively. Similarly, the reaction of 1 equivalent of CDI with at least 3 equivalents of acetaldehyde yields 1,1'-(prop-1-ene-1,1-diyl)bis(1H-imidazole).

The transformations described herein could allow for alternative chemistries related to catalysis or carbamide-based pharmaceutical development and drug delivery. Carbamides are contained within fungicides (i.e., prochloraz), barbiturates, as well as anti-inflammatory, anti-microbial, and anti-convulsant compounds (38-41). This chemistry could be utilized in the design and expansion of pharmaceuticals containing these functional features, or employed in the grafting or tethering of pharmaceuticals for investigative drug delivery methodologies. Furthermore, the described vinylidene derivatives are polymerizable, leading to new forms of poly(azoles) or cationic poly(azolium) polyelectrolytes with an unprecedented architecture and controllable ionizable content, in contrast to the architectures of poly(vinylimidazole), poly(vinylimidazolium), (i.e., poly(ionic liquids)) and ionenes (42, 43). Cationic polyelectrolytes and ionenes find use in a range of applications, including batteries, biocompatible materials, as antimicrobial/antifungal substrates, and in separation processes (44, 45).

Methods for Synthesizing Compounds of Formula I or Formula III

The present disclosure provides methods for synthesizing vinylidene or alkene compounds substituted at their open valencies with one or more nitrogen containing substituents. "Vinylidene" as used herein refers to a 1,1-ethenediyl (C═CH$_2$) moiety.

Thus, in one aspect, the present disclosure provides a method for synthesizing a compound of Formula VI

the method comprising reacting a compound of Formula II

with a compound of Formula VII

or an acetal derivative or a polyacetal derivative thereof, at elevated temperature to form the compound of Formula VI;
wherein:
$R^1$ is selected from hydrogen, alkyl, cycloalkyl, heterocycle, aryl, heteroaryl, $OR^3$, $SR^3$, and $NR^4R^5$, each of which may be optionally substituted with one or more Z groups;
$R^2$ is $NR^6R^7$;
$R^3$ is selected from alkyl, cycloalkyl, heterocycle, aryl, and heteroaryl, each of which may be optionally substituted with one or more Z groups;
$R^4$ and $R^5$ are independently selected from hydrogen, alkyl, cycloalkyl, heterocycle, aryl, and heteroaryl, each of which may be optionally substituted with one or more Z groups; or
$R^4$ and $R^5$ may be brought together with the nitrogen to which they are attached to form a heterocycle ring or a heteroaryl ring, wherein said heterocycle ring or heteroaryl ring may be optionally substituted with one or more Z groups;
$R^6$ and $R^7$ are independently selected hydrogen, alkyl, cycloalkyl, heterocycle, aryl, and heteroaryl, each of which may be optionally substituted with one or more Z groups; or
$R^6$ and $R^7$ may be brought together with the nitrogen to which they are attached to form a heterocycle ring or a heteroaryl ring, wherein said heterocycle ring or heteroaryl ring may be optionally substituted with one or more Z groups;

$R^{20}$ is selected from hydrogen, alkyl, cycloalkyl, heterocycle, aryl, and heteroaryl, each of which may be optionally substituted with one or more Z groups; and Z is independently selected at each occurrence from alkyl, haloalkyl, alkoxy, alkenyl, alkynyl, aryl, heteroaryl, cycloalkyl, heterocycle, aldehyde, amino, carboxylic acid, ester, ether, halo, hydroxy, keto, nitro, cyano, azido, silyl, sulfooxo, sulfonyl, sulfone, sulfoxide, sulfonylamino, and thiol.

An "acetal derivative" as used herein refers to a compound having the formula $R^{20}CH(OR^{21})(OR^{22})$, wherein $R^{21}$ and $R^{22}$ may each be selected from alkyl, cycloalkyl, heterocycle, aryl, and heteroaryl, each of which may be unsubstituted or optionally substituted as defined herein, or wherein $R^{21}$ and $R^{22}$ are brought together with the atoms to which they are attached to form an optionally substituted heterocycle ring, and $R^{10}$ is as defined herein. Representative acetal derivatives may include dimethoxymethane and diethoxyethane. A "polyacetal derivative" as used herein refers to a compound having two or more monomeric units having the structure —O—$CHR^{20}$—O—, wherein $R^{20}$ is as defined herein. In some embodiments, the polyacetal derivative may comprise a trioxolane, for example 1,3,5-trioxolane or paraldehyde. In some embodiments, the polyacetal derivative may comprise a polymer, for example paraformaldehyde.

In some embodiments, the molar ratio of the compound of Formula VII to the compound of Formula II is about 2:1, 2.5:1, 3:1, 3.5:1, or 4:1. In typical embodiments, the molar ratio of the compound of Formula VII to the compound of Formula II in the reaction is about 3:1.

In some embodiments, the compound of Formula II is reacted with the compound of Formula VII at a temperature of about 50° C. or more, about 60° C. or more, about 70° C. or more, about 80° C. or more, about 90° C. or more, about 100° C. or more, about 110° C. or more, or about 120° C. or more. In some embodiments, the compound of Formula II is reacted with the compound of Formula VII at a temperature of about 50° C., 55° C., 60° C., 65° C., 70° C., 75° C., 80° C., 85° C., 90° C., 95° C., 100° C., 105° C., 110° C., 115° C., 120° C. or more. In some embodiments, the compound of Formula II is reacted with the compound of Formula VII at a temperature from about 50° C. to about 120° C., for example from about 60° C. to about 120° C., about 70° C. to about 120° C., about 80° C. to about 120° C., about 90° C. to about 120° C., about 100° C. to about 120° C., about 110° C. to about 120° C., about 50° C. to about 110° C., about 60° C. to about 110° C., about 70° C. to about 110° C., about 80° C. to about 110° C., about 90° C. to about 110° C., about 100° C. to about 110° C., about 50° C. to about 100° C., about 60° C. to about 100° C., about 70° C. to about 100° C., about 80° C. to about 100° C., about 90° C. to about 100° C., about 50° C. to about 90° C., about 60° C. to about 90° C., about 70° C. to about 90° C., about 80° C. to about 90° C., about 50° C. to about 80° C., about 60° C. to about 80° C., about 70° C. to about 80° C., about 50° C. to about 70° C., about 60° C. to about 70° C., or about 50° C. to about 60° C.

In some embodiments, the compound of Formula II may be reacted with the compound of Formula VII for a period of time of about 1 hour, about 2 hours, about 3 hours, about 4 hours, about 5 hours, about 6 hours, about 12 hours, about 18 hours, about 24 hours, about 36 hours or about 48 hours or more. In typical embodiments, the compound of Formula II may be reacted with the compound of Formula VII for about 24 hours.

In another aspect, the present disclosure provides a method for synthesizing a compound of Formula I

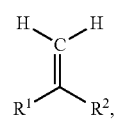

(I)

the method comprising reacting a compound of Formula II

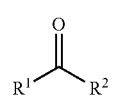

(II)

with paraformaldehyde at elevated temperature to form the compound of Formula I;

wherein:

$R^1$ is selected from hydrogen, alkyl, cycloalkyl, heterocycle, aryl, heteroaryl, $OR^3$, $SR^3$, and $NR^4R^5$, each of which may be optionally substituted with one or more Z groups;

$R^2$ is $NR^6R^7$;

$R^3$ is selected from alkyl, cycloalkyl, heterocycle, aryl, and heteroaryl, each of which may be optionally substituted with one or more Z groups;

$R^4$ and $R^5$ are independently selected from hydrogen, alkyl, cycloalkyl, heterocycle, aryl, and heteroaryl, each of which may be optionally substituted with one or more Z groups; or $R^4$ and $R^5$ may be brought together with the nitrogen to which they are attached to form a heterocycle ring or a heteroaryl ring, wherein said heterocycle ring or heteroaryl ring may be optionally substituted with one or more Z groups;

$R^6$ and $R^7$ are independently selected hydrogen, alkyl, cycloalkyl, heterocycle, aryl, and heteroaryl, each of which may be optionally substituted with one or more Z groups; or $R^6$ and $R^7$ may be brought together with the nitrogen to which they are attached to form a heterocycle ring or a heteroaryl ring, wherein said heterocycle ring or heteroaryl ring may be optionally substituted with one or more Z groups; and Z is independently selected at each occurrence from alkyl, haloalkyl, alkoxy, alkenyl, alkynyl, aryl, heteroaryl, cycloalkyl, heterocycle, aldehyde, amino, carboxylic acid, ester, ether, halo, hydroxy, keto, nitro, cyano, azido, silyl, sulfooxo, sulfonyl, sulfone, sulfoxide, sulfonylamino, and thiol.

"Paraformaldehyde" as used herein refers to a polyoxymethylene polymer having the formula

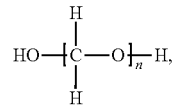

wherein n may range from 5 to 500, more typically ranging from 8 to 100. Paraformaldehyde is a readily obtainable material that is available from numerous chemical suppliers.

In some embodiments, the molar ratio of paraformaldehyde to the compound of Formula II is about 2:1, 2.5:1, 3:1, 3.5:1, or 4:1 based upon the molecular weight of the monomeric unit of paraformaldehyde (MW=30.03). In typical embodiments, the molar ratio of paraformaldehyde to the compound of Formula II in the reaction is about 3:1 based upon the molecular weight of the monomeric unit of paraformaldehyde.

In some embodiments, the compound of Formula II is reacted with paraformaldehyde at a temperature of about 50° C. or more, about 60° C. or more, about 70° C. or more, about 80° C. or more, about 90° C. or more, about 100° C. or more, about 110° C. or more, or about 120° C. or more. In some embodiments, the compound of Formula II is reacted with paraformaldehyde at a temperature of about 50° C., 55° C., 60° C., 65° C., 70° C., 75° C., 80° C., 85° C., 90° C., 95° C., 100° C., 105° C., 110° C., 115° C., 120° C. or more. In some embodiments, the compound of Formula II is reacted with paraformaldehyde at a temperature from about 50° C. to about 120° C., for example from about 60° C. to about 120° C., about 70° C. to about 120° C., about 80° C. to about 120° C., about 90° C. to about 120° C., about 100° C. to about 120° C., about 110° C. to about 120° C., about 50° C. to about 110° C., about 60° C. to about 110° C., about 70° C. to about 110° C., about 80° C. to about 110° C., about 90° C. to about 110° C., about 100° C. to about 110° C., about 50° C. to about 100° C., about 60° C. to about 100° C., about 70° C. to about 100° C., about 80° C. to about 100° C., about 90° C. to about 100° C., about 50° C. to about 90° C., about 60° C. to about 90° C., about 70° C. to about 90° C., about 80° C. to about 90° C., about 50° C. to about 80° C., about 60° C. to about 80° C., about 70° C. to about 80° C., about 50° C. to about 70° C., about 60° C. to about 70° C., or about 50° C. to about 60° C.

In some embodiments, the compound of Formula II may be reacted with paraformaldehyde for a period of time of about 1 hour, about 2 hours, about 3 hours, about 4 hours, about 5 hours, about 6 hours, about 12 hours, about 18 hours, about 24 hours, about 36 hours, about 48 hours or more. In typical embodiments, the compound of Formula II may be reacted with paraformaldehyde for about 24 hours.

In some embodiments, the reactions described herein may occur in the presence of a solvent. Representative examples of solvents which may be used include, but are not limited to, pentane, cyclopentane, hexane, cyclohexane, benzene, carbon tetrachloride, toluene, 1,4-dioxane, diethyl ether, chloroform, dichloromethane, tetrahydrofuran, ethyl acetate, acetone, dimethylformamide, acetonitrile, dimethylsulfoxide, nitromethane, propylene carbonate, formic acid, n-butanol, isopropyl alcohol, n-propanol, ethanol, methanol, acetic acid, or water. In typical embodiments, the solvent may comprise acetonitrile.

The above reaction may be performed in any reaction vessel that is appropriate for the type of reagents/reactants and solvents used and the scale of the reaction performed. In embodiments where the reaction is performed at a temperature above the boiling point of the solvent or any of the reagents used, the reaction may be performed in a pressure reactor, for example a standard glass pressure reactor, a fisher porter tube or vessel, or a metal pressure reactor. Suitable reaction vessels are commercially available and may be readily selected by one of ordinary skill in the art for the particular conditions to be applied. In some embodiments, the reaction may be performed under microwave irradiation in order to induce the elevated temperature required; in such embodiments the reaction may be performed in a microwave synthesizer. Microwave synthesizers are commercially available from multiple suppliers.

In some embodiments, $R^1$ is hydrogen. In some embodiments, $R^1$ is alkyl, for example methyl, ethyl, or isopropyl. In some embodiments, $R^1$ is cycloalkyl, for example cyclopropyl, cyclobutyl, cyclopentyl, or cyclohexyl. In some embodiments, $R^1$ is heterocycle. In some embodiments, $R^1$ is aryl, for example phenyl. In some embodiments, $R^1$ is heteroaryl. In some embodiments, $R^1$ is $OR^3$, for example methoxy or ethoxy. In some embodiments, $R^1$ is $SR^3$. In some embodiments, $R^1$ is $NR^4R^5$.

In some embodiments, $R^{20}$ is hydrogen. In some embodiments, $R^{20}$ is alkyl, for example methyl, ethyl, or isopropyl. In some embodiments, $R^{20}$ is cycloalkyl, for example cyclopropyl, cyclobutyl, cyclopentyl, or cyclohexyl. In some embodiments, $R^{20}$ is heterocycle. In some embodiments, $R^{20}$ is aryl, for example phenyl. In some embodiments, $R^{20}$ is heteroaryl.

In some embodiments, $NR^4R^5$ is selected from:

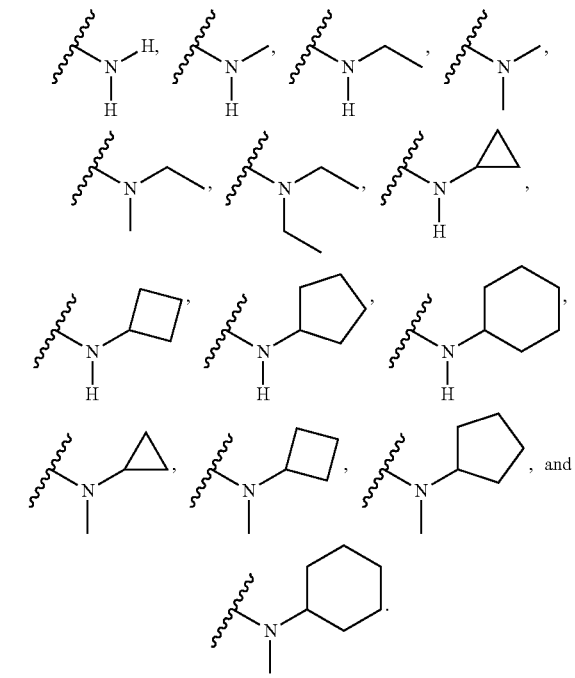

In some embodiments, $NR^4R^5$ is selected from:

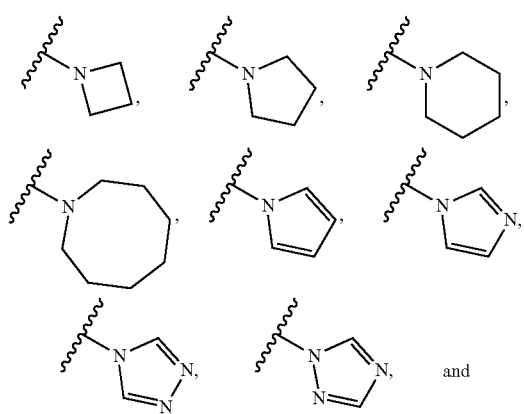

-continued

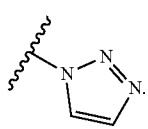

Representative examples of compounds of Formula II include, but are not limited to:

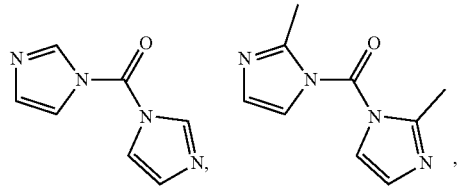

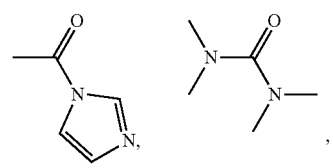

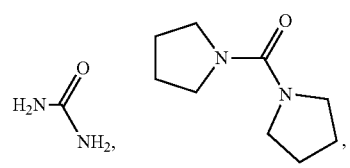

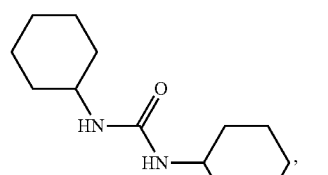

and

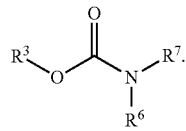

Representative examples of compounds of Formula I or Formula VI as produced by the present methods include, but are not limited to:

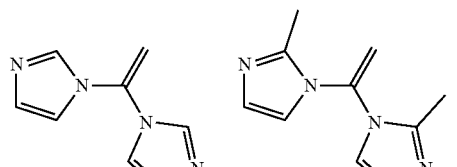

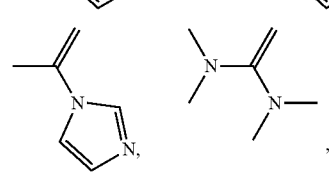

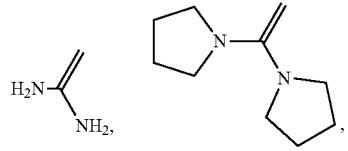

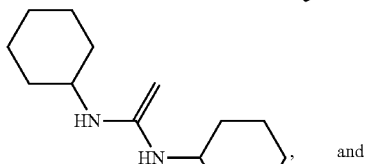

and

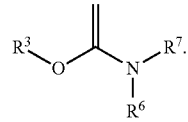

A Representative example of a compound of Formula VI as provided by the present methods includes, but is not limited to:

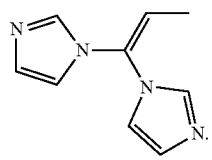

In another aspect, a compound of Formula I-a is provided:

(I-a)

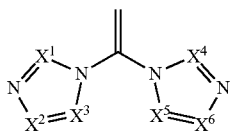

wherein $X^1$, $X^2$, $X^3$, $X^4$, $X^5$, and $X^6$ are each selected from N, CH, or C—Z, wherein at least one of $X^1$, $X^2$, $X^3$, $X^4$, $X^5$, and $X^6$ in Formula I-a is C—Z, wherein no more than one of $X^1$, $X^2$, and $X^3$, in Formula I-a is N, wherein no more than one of $X^4$, $X^5$, $X^6$ in Formula I-a is N, and Z is as defined herein.

In another aspect, a compound of Formula VI-a is provided:

(VI-a)

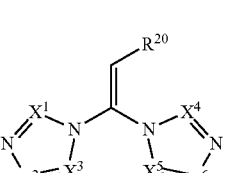

wherein $X^1$, $X^2$, $X^3$, $X^4$, $X^5$, and $X^6$ are each selected from N, CH, or C—Z, wherein at least one of $X^1$, $X^2$, $X^3$, $X^4$, $X^5$, and $X^6$ in Formula I-a is C—Z, wherein no more than one of $X^1$, $X^2$, and $X^3$, in Formula I-a is N, wherein no more than one of $X^4$, $X^5$, $X^6$ in Formula I-a is N, and Z is as defined herein.

Uses of Compounds of Formula I

Uses of the compounds of Formula I may be readily identified by those of ordinary skill in the art. Representative examples are provided below that are in no way meant to limit the potential applications of the compounds synthesized by the methods described herein.

In one aspect, the compounds of Formula I as prepared herein may be use in the preparation of cationic derivatives which may find use as ionic liquids or in the preparation of charged polymers. Compounds of Formula I may be, for example, alkylated at available nitrogen positions under standard alkylating conditions or may be substituted with an aryl or heteroaryl group using cross-coupling conditions such as the Buchwald-Hartwig coupling that would be readily known to those of skill in the art.

Thus in one representative aspect, compounds of Formula III are provided:

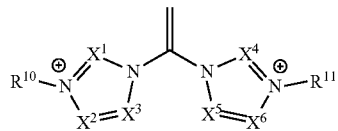

(III)

and one or more anions balancing the charge of the compound of Formula III;

wherein $R^{10}$ and $R^{11}$ are independently selected from alkyl, cycloalkyl, aryl, or heteroaryl, each of which may be optionally substituted with one or more Z groups;

wherein $X^1$, $X^2$, $X^3$, $X^4$, $X^5$ and $X^6$ are independently selected from N, C—H, or C—Z;

wherein no more than one of $X^1$, $X^2$, and $X^3$ in Formula III are N;

wherein no more than one of $X^4$, $X^5$, and $X^6$ in Formula III are N;

and all other variables are as defined herein.

Representative examples of compounds of Formula III include, but are not limited to:

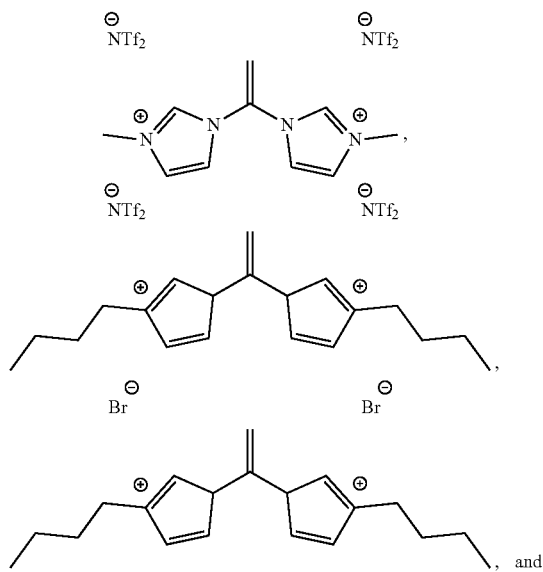

and

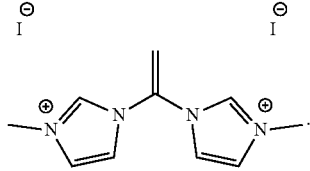

In another aspect, compounds of Formula III-a are provided:

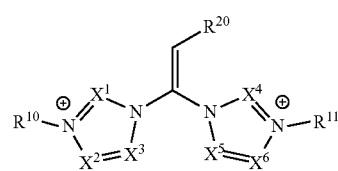

(III-a)

and one or more anions balancing the charge of the compound of Formula III-a;

wherein all variables are as defined herein.

In another representative aspect, compound of Formula IV are provided:

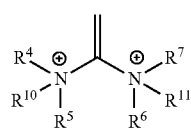

(IV)

and one or more anions balancing the charge of the compound of Formula IV;

wherein all variables are as defined herein.

In another representative aspect, compound of Formula IV-a are provided:

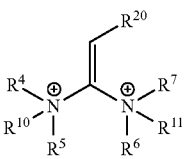

(IV-a)

and one or more anions balancing the charge of the compound of Formula IV-a;

wherein all variables are as defined herein.

The above compounds of Formula III, III-a, IV, and IV-a are cationic and are typically found paired with one or more anions in their natural state. Representative examples of such anions include, but are not limited to, halides (such as chloride, bromide, fluoride, or iodide), hydroxide, bis(trifluoromethanesulfonyl)amide anion, hexafluorophosphate anion, trifluoromethanesulfonate anion, dicyanamide anion, tetrafluoroborate anion, thiocyanate anion, nitrate anion, sulfonate anion, methylsulfate anion, or combinations thereof.

In another aspect, the vinylidene compounds of Formula I described herein may be used in the synthesis of polymers.

Thus in another representative aspect, a polymer is provided comprising one or more monomeric units selected from Formula V, Formula V-a, or combinations thereof:

(V)

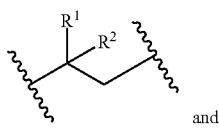

and (V-a)

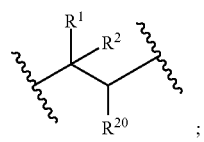

;

wherein $R^1$, $R^2$, and $R^{20}$ are as defined herein.

In another aspect, a polymer is provided comprising one or more monomeric units of Formula V-b:

(V-b)

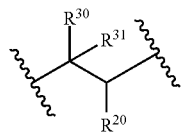

and one or more anions balancing the charge of the compound of Formula V-b;

$R^{30}$ is

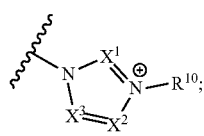

$R^{31}$ is

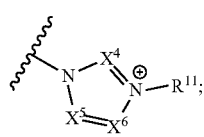

and wherein all other variables are as defined herein.

A representative polymer includes, but is not limited to, Polymer 1:

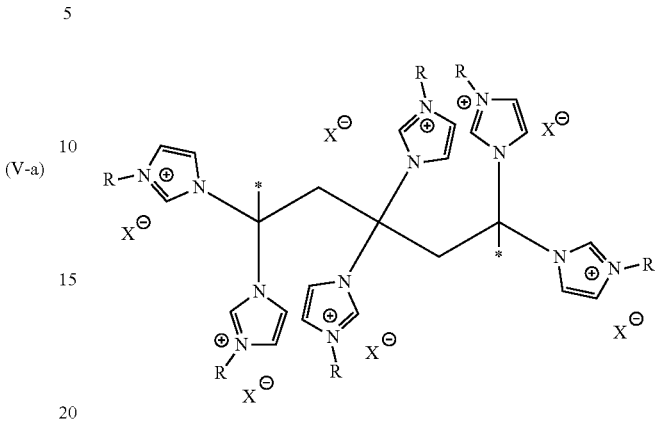

wherein X comprises an anion.

A number of embodiments of the disclosure have been described. Nevertheless, it will be understood that various modifications may be made without departing from the spirit and scope of the invention. Accordingly, other embodiments are within the scope of the following claims.

By way of non-limiting illustration, examples of certain embodiments of the present disclosure are given below.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Representative Synthetic Procedure for Synthesis of 1,1'-(ethene-1,1-diyl)bis(1H-imidazole) (I)

To a 250 mL heavy-walled round-bottom pressure vessel (Ace Glass) was added CDI (10.00 g, 61.7 mmol) and PFA (7.41 g, 247 mmol). The vessel was equipped with a stir bar and acetonitrile (100 mL) was added, and the vessel was sealed with a threaded PTFE cap. The reaction was then heated at 120° C. for 24 h. The reaction mixture was cooled to RT and was precipitated and stirred in 200 mL of DI water for 24 h. The product was isolated via vacuum filtration to yield I as an off-white powder (5.44 g 55%). mp: 185-189° C.; $^1$H NMR (500 MHz, DMSO-d6): δ 7.95 (s, 2H), 7.41 (s, 2H) 6.92 (s, 2H) 6.23 (s, 2H); $^{13}$C NMR (125 MHz, DMSO-d6): δ 138, 130, 120, 108, 55; HRMS (m/z): [M]$^+$ calcd. for $C_8H_8N_4$, 160.0749; found, 160.0744.

Other representative compounds prepared according to these methods are provided in Scheme 1 below:

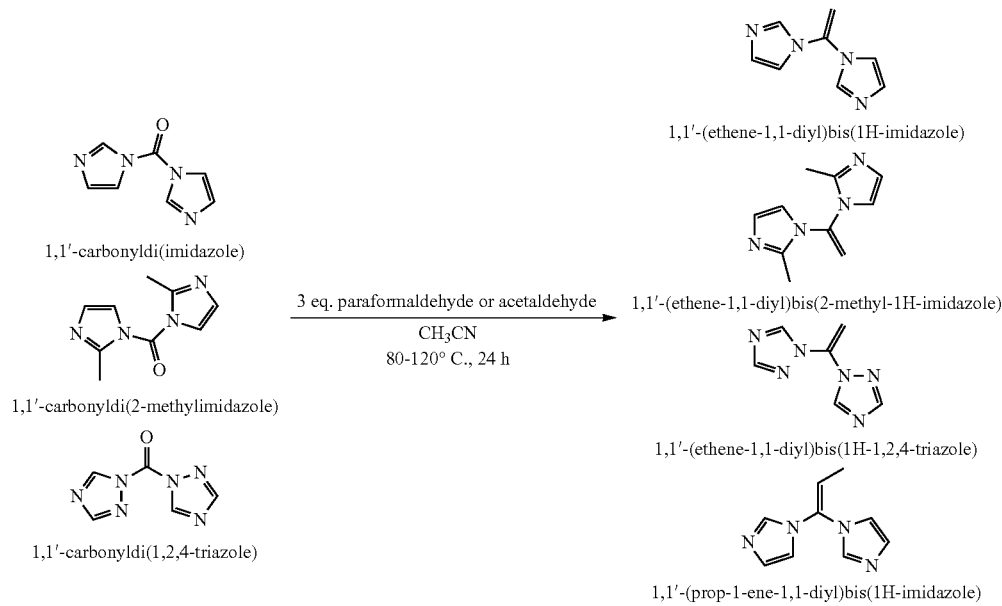

Higher order alkene derivatives may be formed according to the procedure described in the following representative scheme:

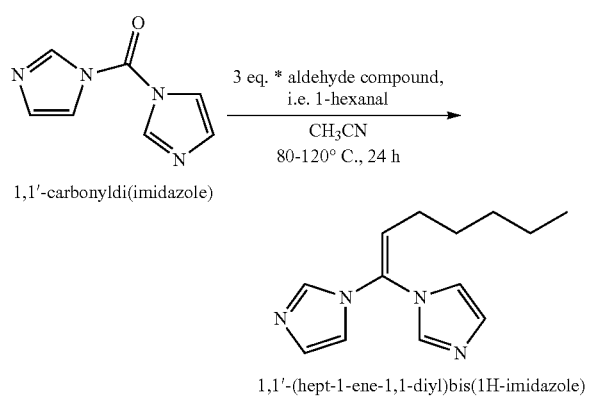

Figure 2:
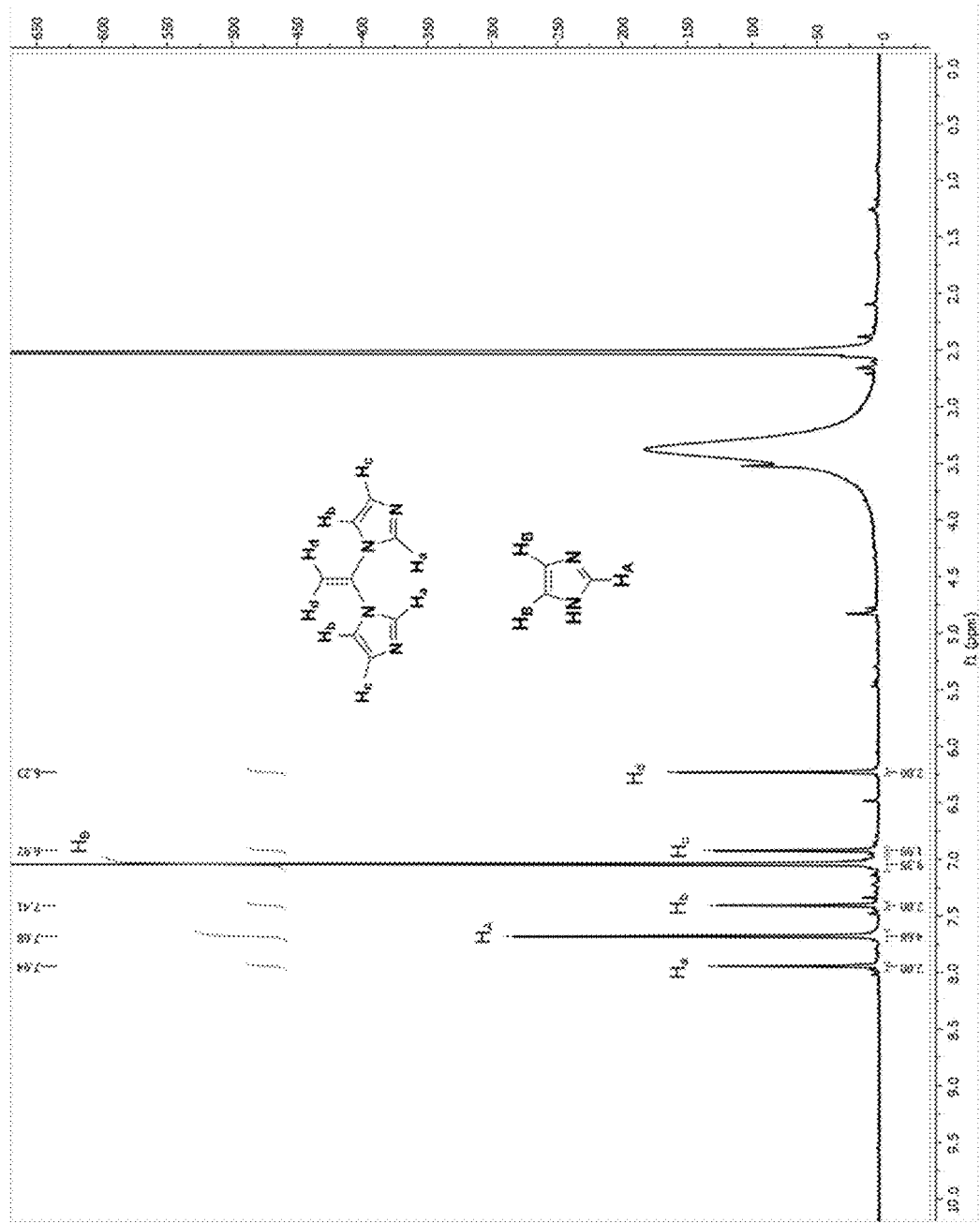
FIG. 2 is a final $^1$H-NMR (500 MHz, $d_6$-DMSO) of 1,1'-(ethene-1,1-diyl)bis(1H-imidazole) product formed from 1,1'-carbonyldi(imidazole) with only 2 equivalents of paraformaldehyde.
Figure 3:
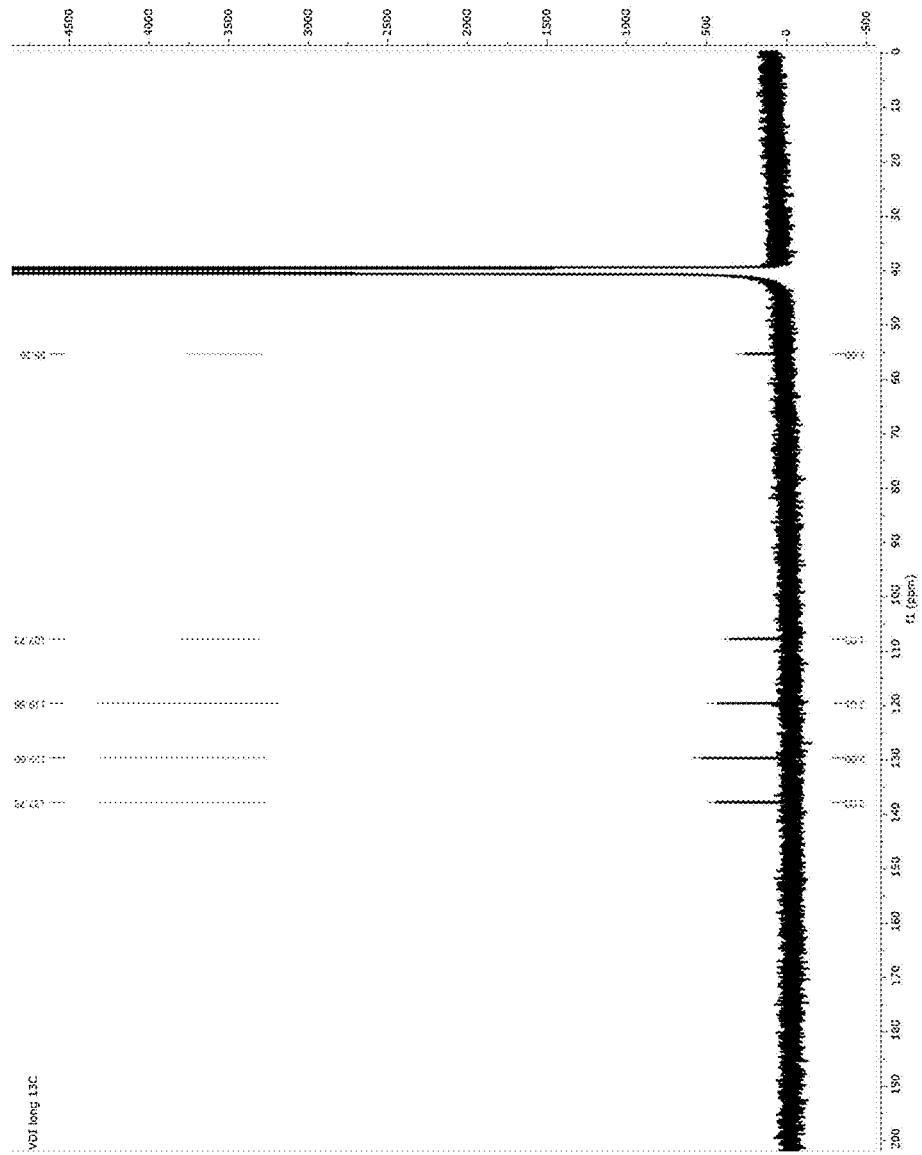
FIG. 3 is a $^{13}$C-NMR (500 MHz, $d_6$-DMSO) of 1,1'-(ethene-1,1-diyl)bis(1H-imidazole) product.
Figure 4:
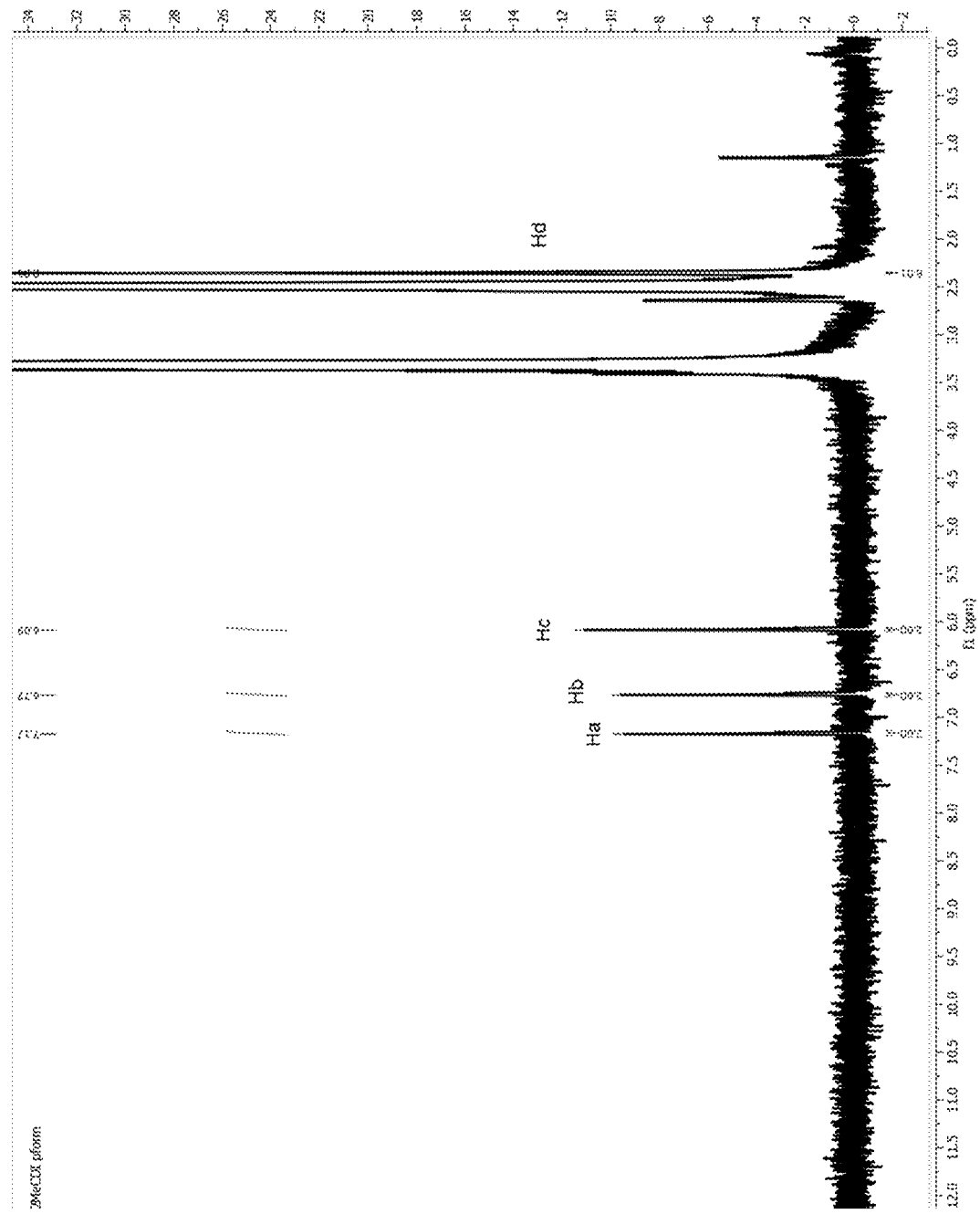
FIG. 4 is a $^1$H-NMR (500 MHz, $d_6$-DMSO) of 1,1'-(ethene-1,1-diyl)bis(2-methyl-1H-imidazole) product.
Figure 5:
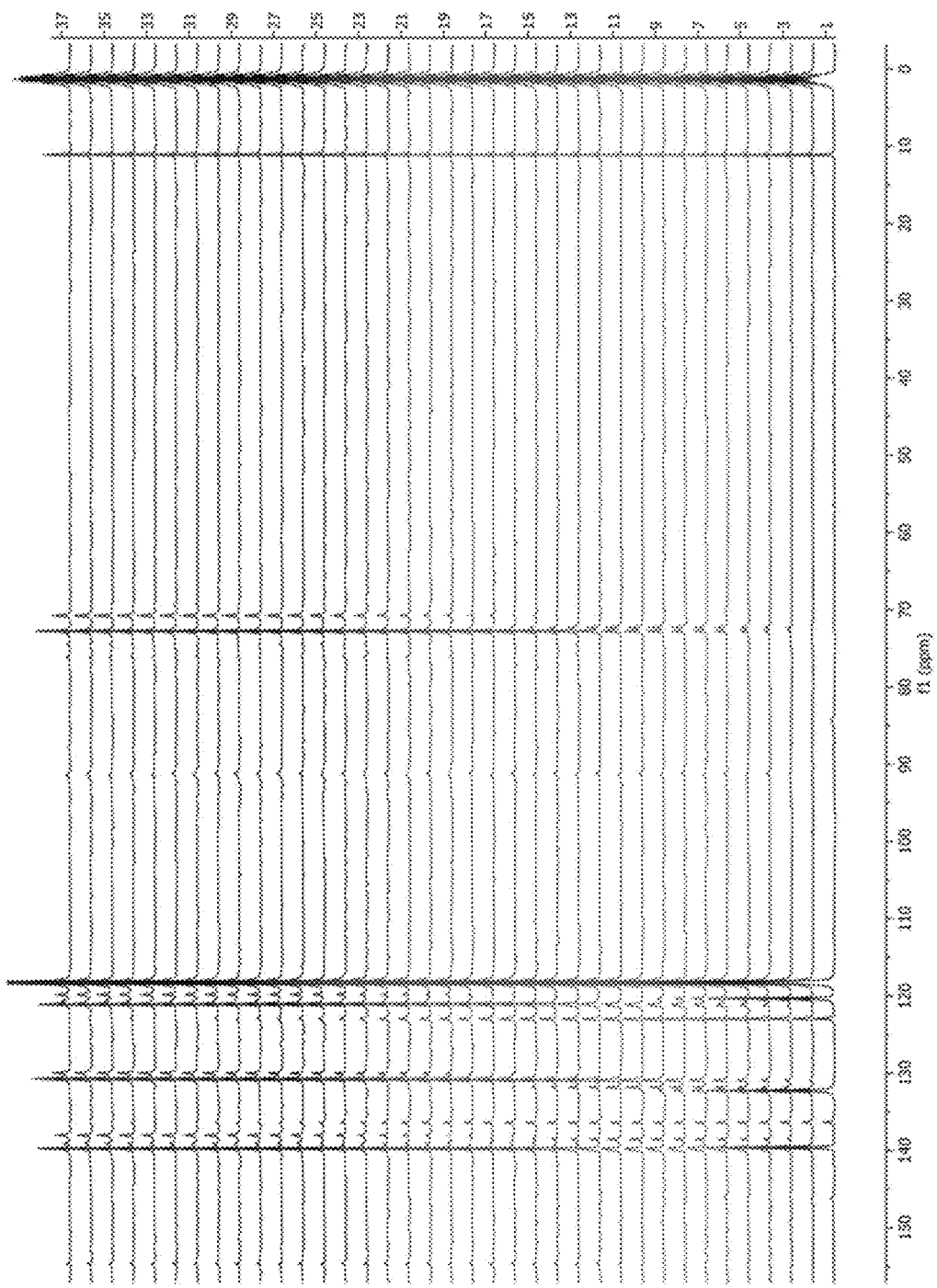
FIG. 5 is $^{13}$C-NMR array for reaction of 1,1'-carbonyldi(imidazole)+4 eq. paraformaldehyde at 70° C. to form 1,1'-(ethene-1,1-diyl)bis(1H-imidazole).
Figure 6:
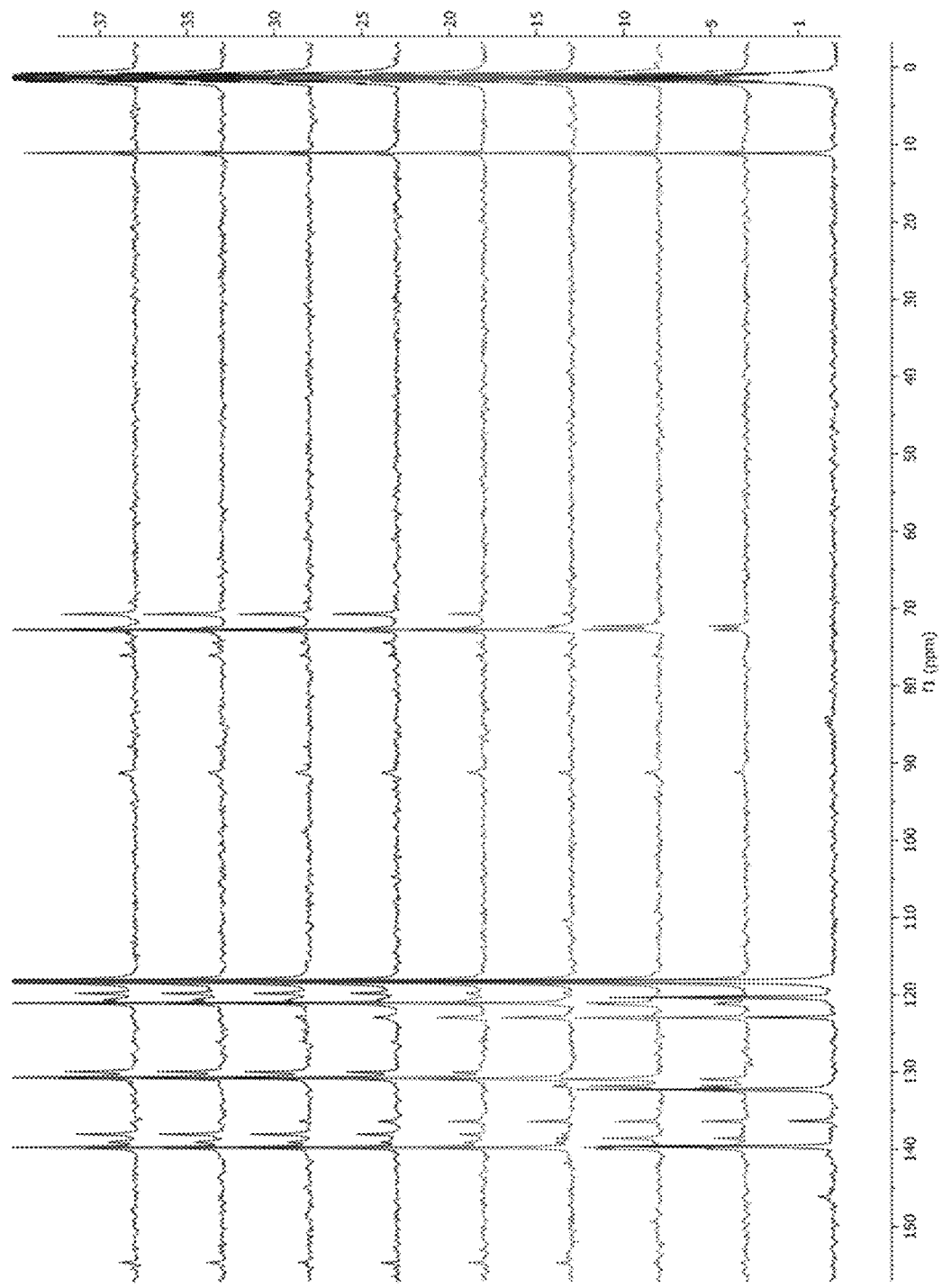
FIG. 6 is selected spectra of $^{13}$C-NMR array shown in FIG. 5.
Figure 7:
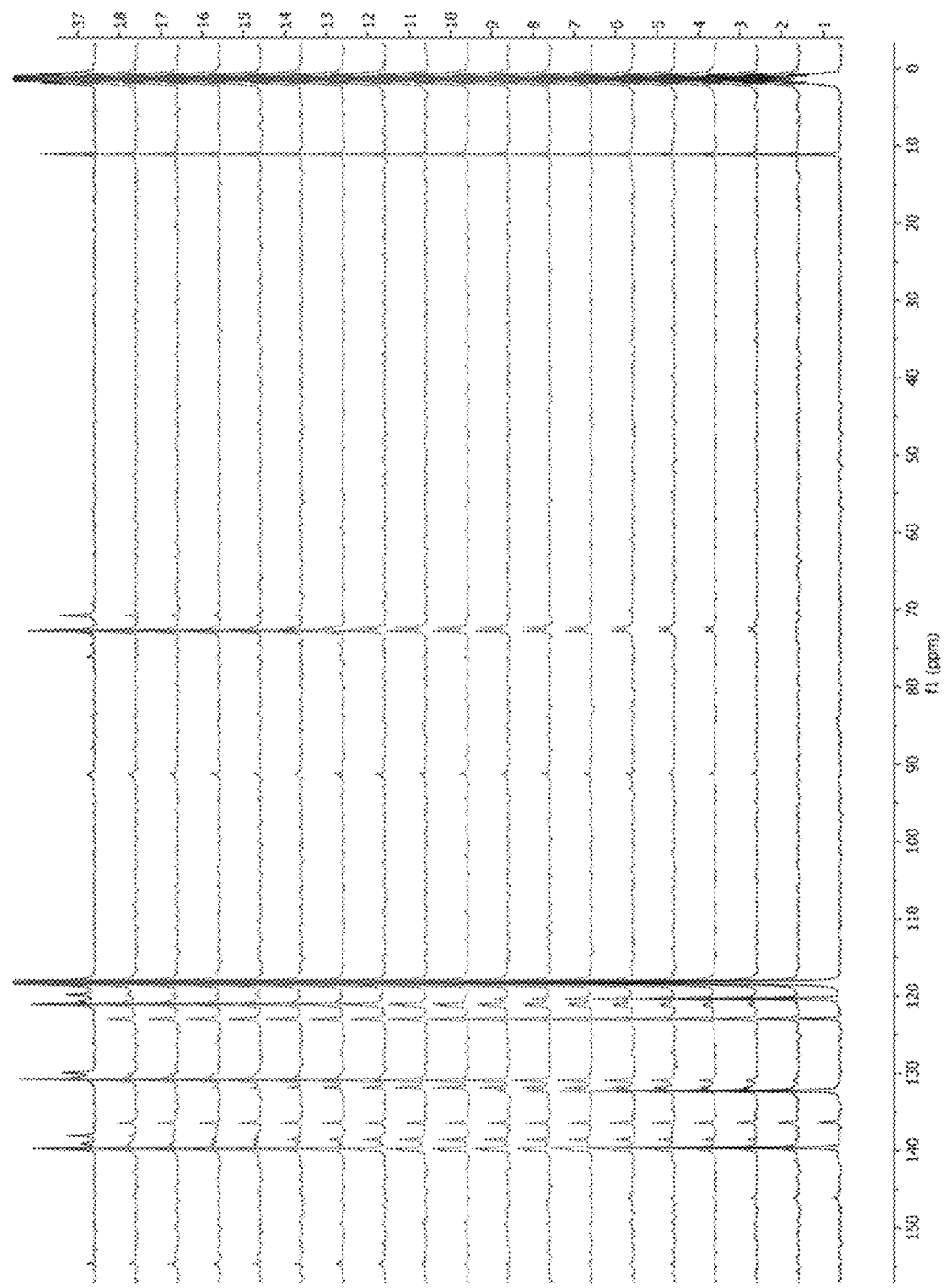
FIG. 7 is selected spectra focused on intermediates of the $^{13}$C-NMR array shown in FIG. 5.
Figure 8:
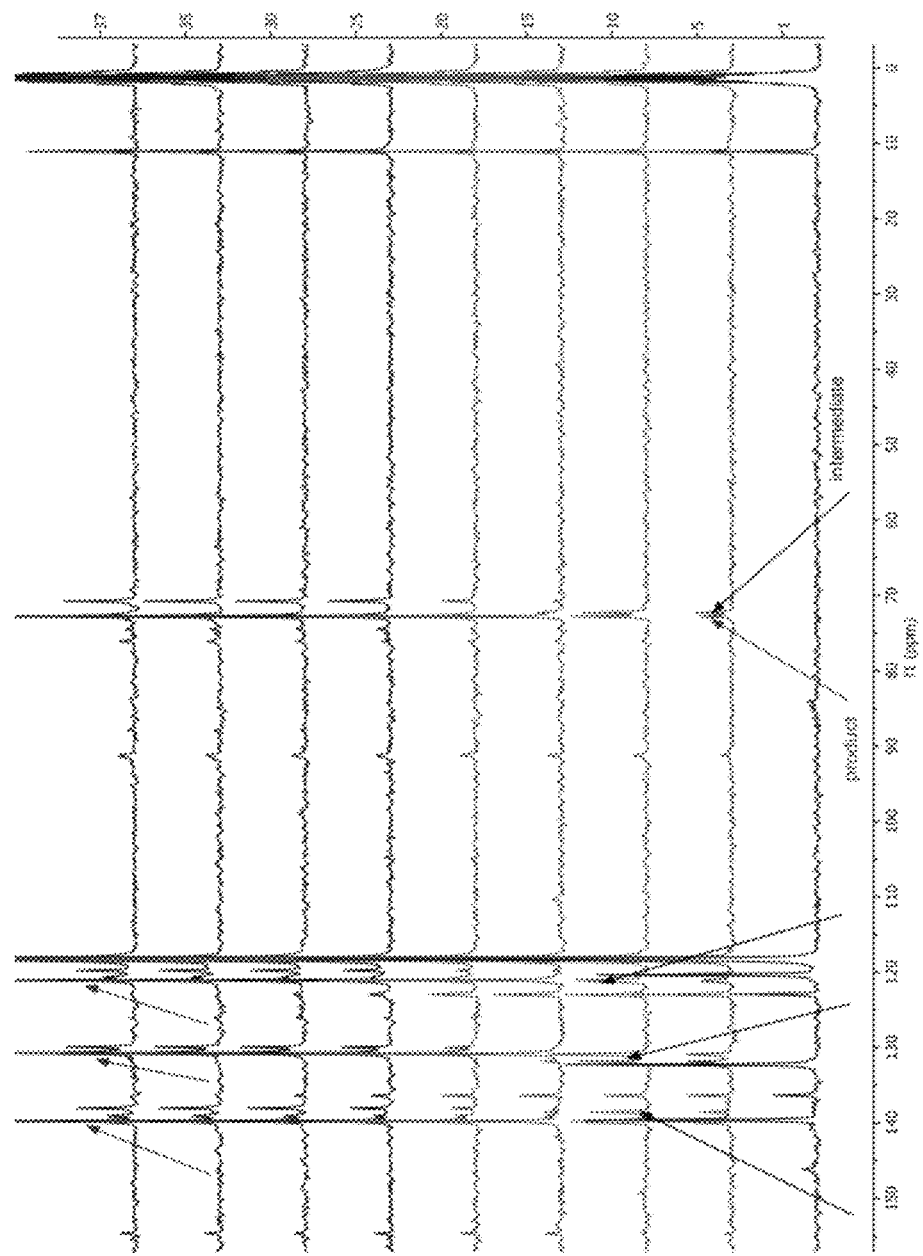
FIG. 8 is the $^{13}$C-NMR array shown in FIG. 5 with identifying arrows.
Figure 9:
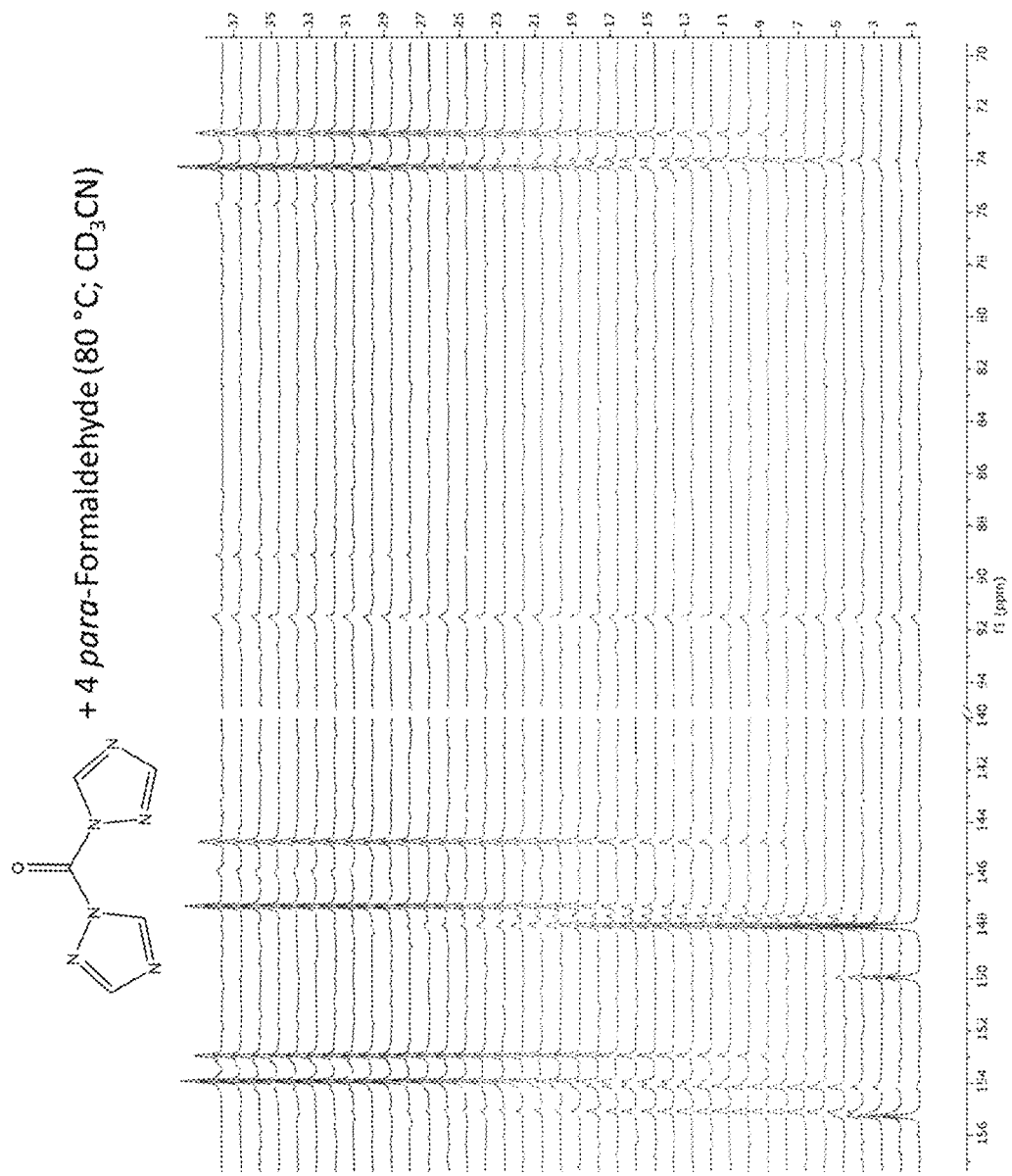
FIG. 9 is $^{13}$C-NMR for reaction of 1,1'-carbonyldi(1,2,4-triazole)+4 eq. paraformaldehyde at 80° C. to form 1,1'-(ethene-1,1-diyl)bis(1H-1,2,4-triazole).
Figure 10:
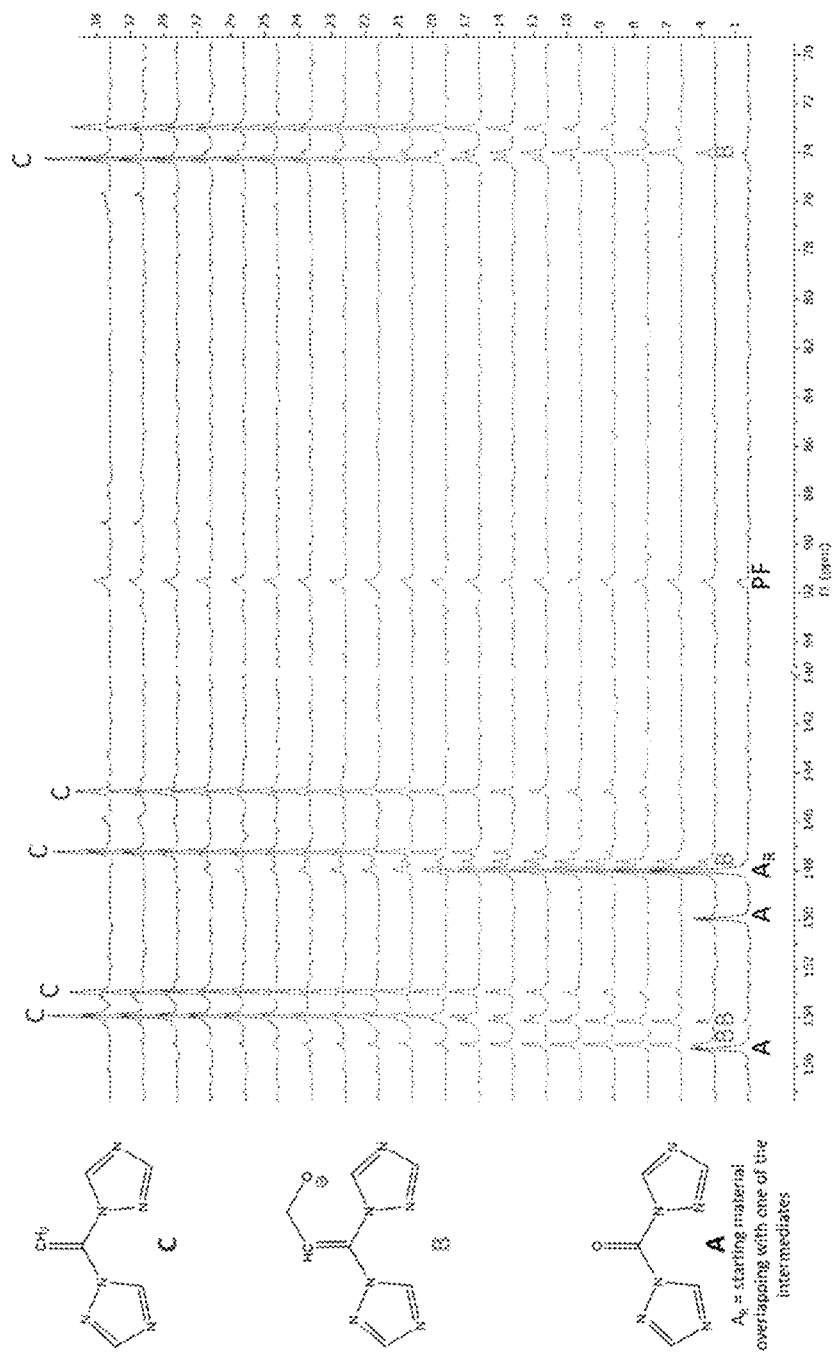
FIG. 10 is $^{13}$C-NMR for reaction of 1,1'-carbonyldi(1,2,4-triazole)+4 eq. paraformaldehyde at 80° C. to form 1,1'-(ethene-1,1-diyl)bis(1H-1,2,4-triazole).
Figure 11:
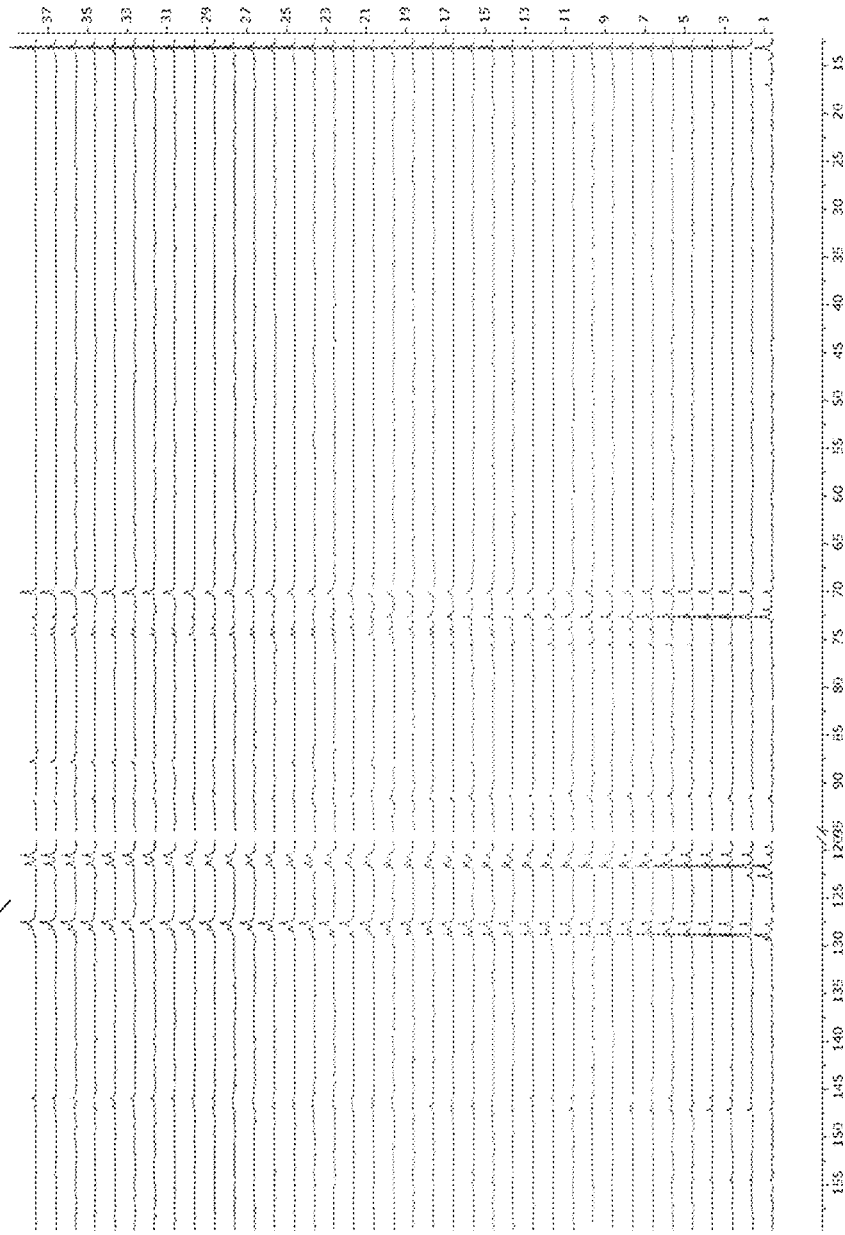
FIG. 11 is $^{13}$C-NMR for reaction of 1,1'-carbonyldi(2-methylimidazole)+4 eq. paraformaldehyde at 80° C. to form 1,1'-(ethene-1,1-diyl)bis(2-methyl-1H-imidazole).
Figure 12:
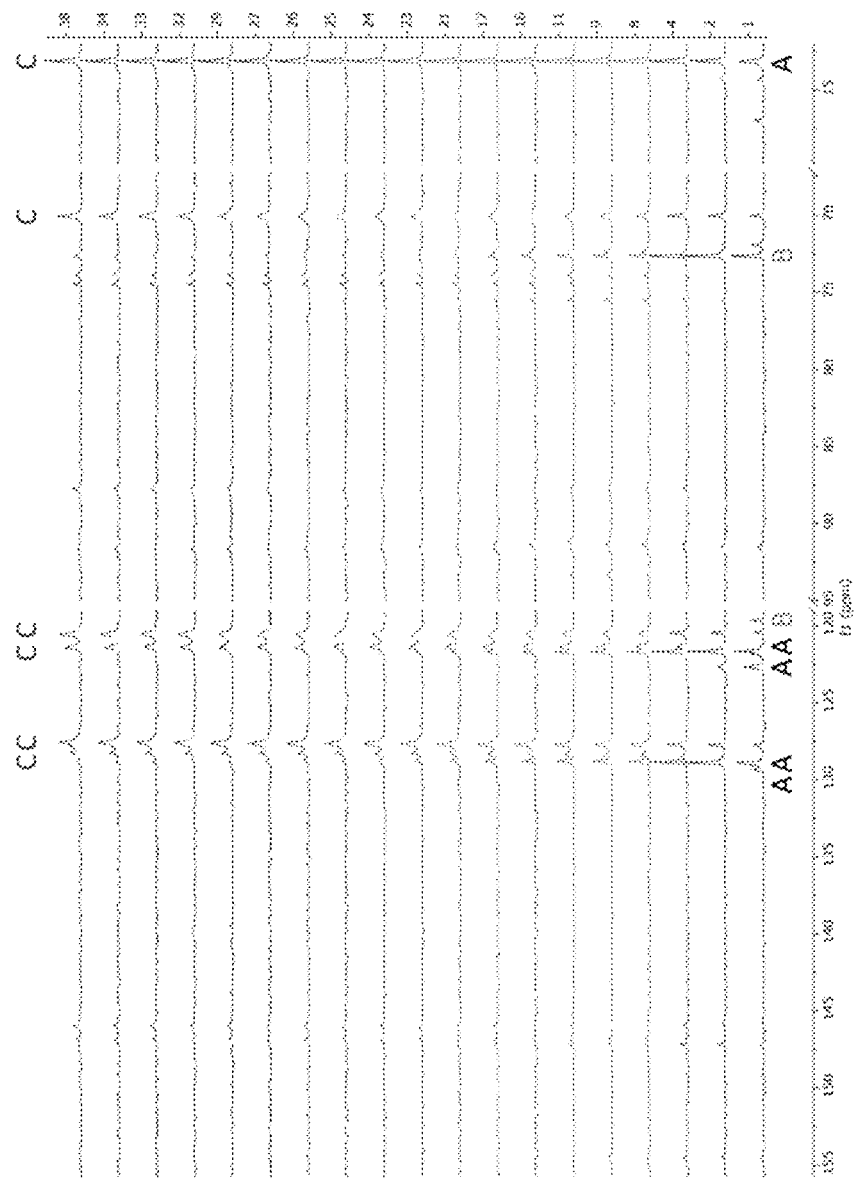
FIG. 12 is $^{13}$C-NMR for reaction of 1,1'-carbonyldi(2-methylimidazole)+4 eq. paraformaldehyde at 80° C. to form 1,1'-(ethene-1,1-diyl)bis(2-methyl-1H-imidazole).
Figure 12:
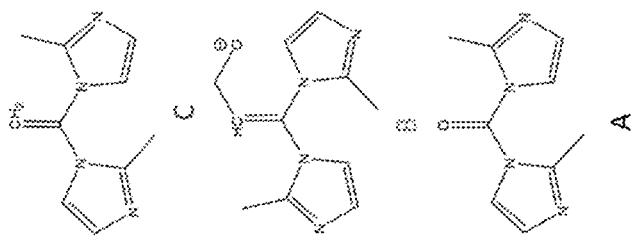
Figure 13:
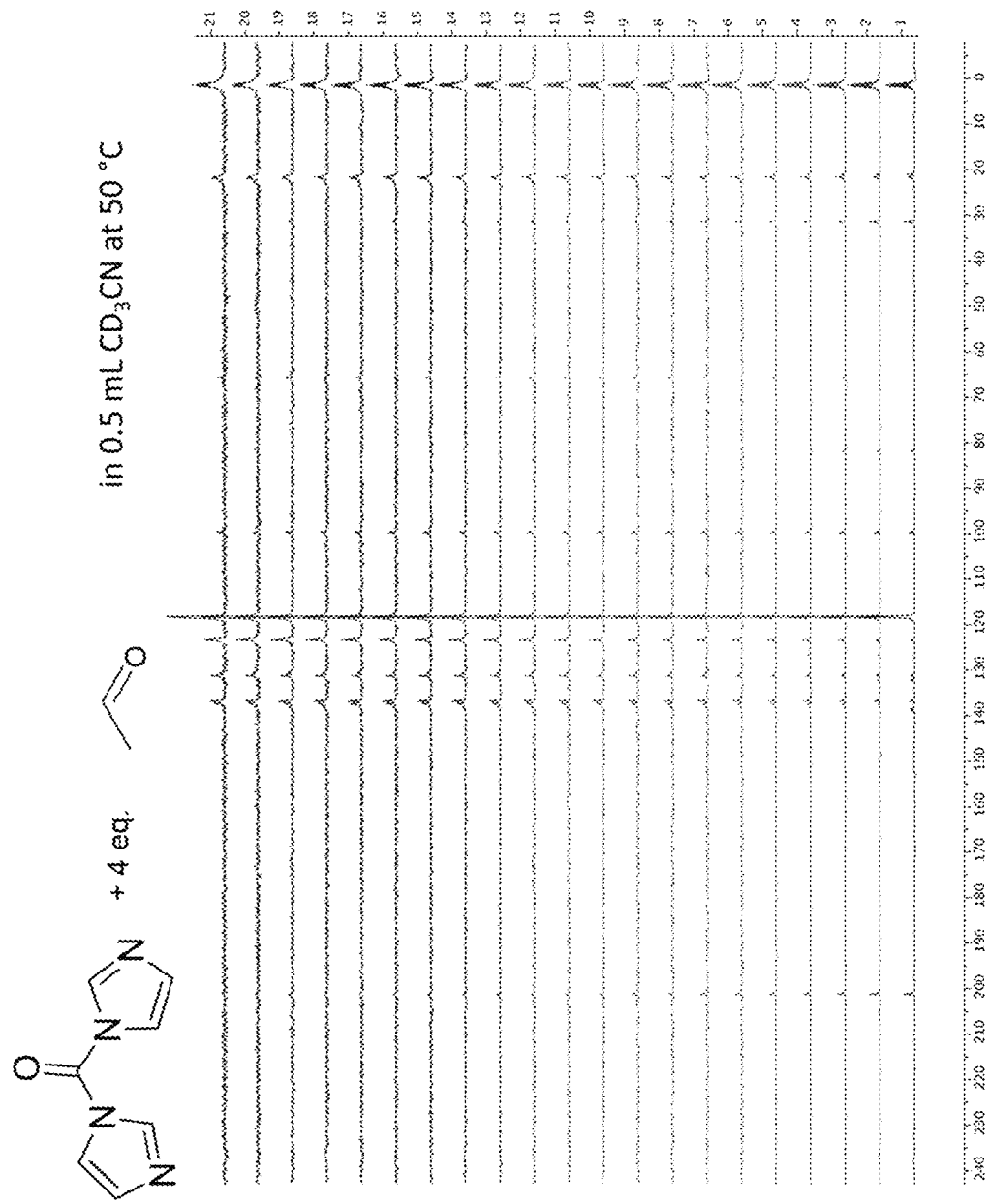
FIG. 13 is $^{13}$C-NMR for reaction of 1,1'-carbonyldi(imidazole)+4 eq. Acetaldehyde at 80° C. to form 1,1'-(prop-1-ene-1,1-diyl)bis(1H-imidazole).
Figure 14:
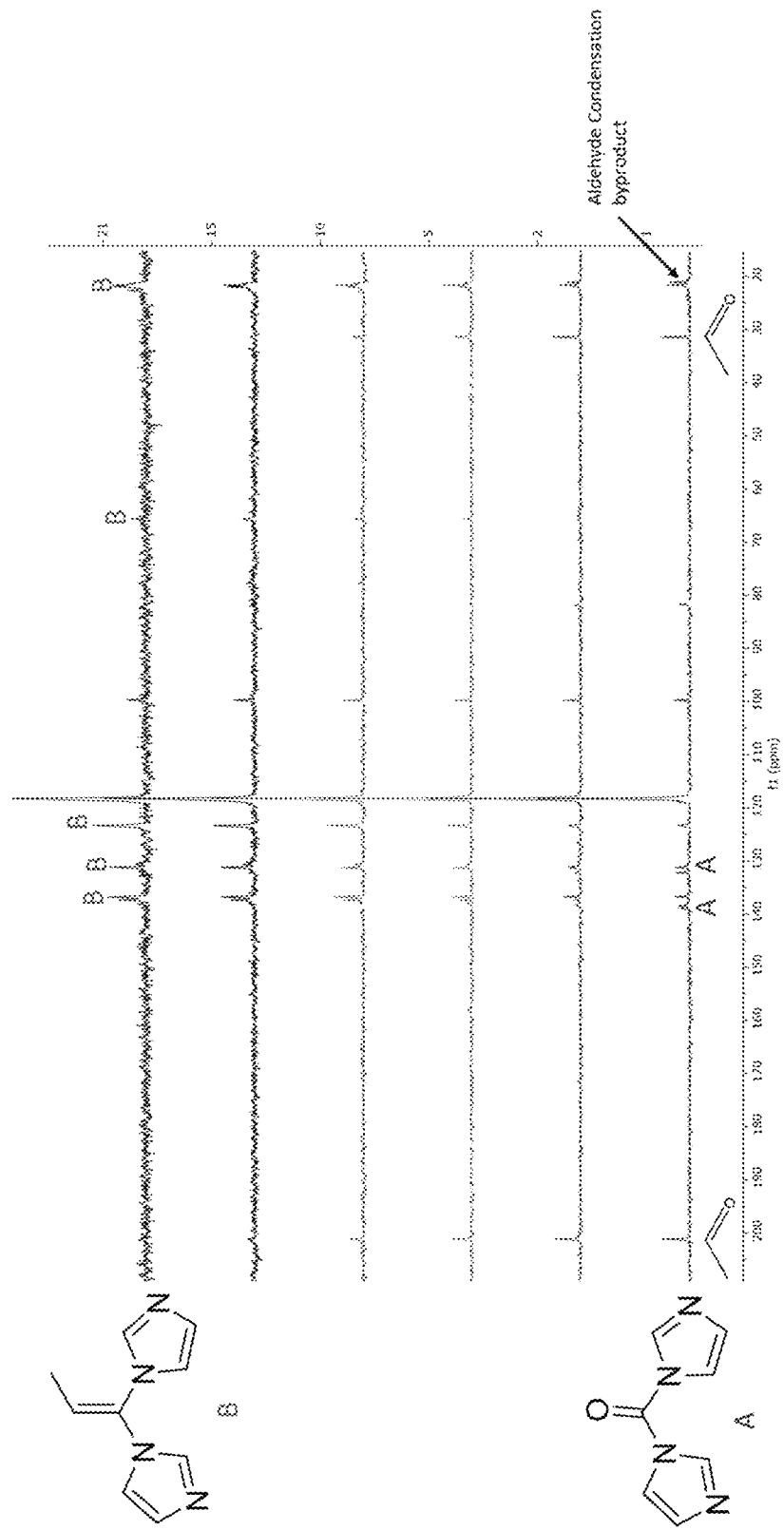
FIG. 14 is $^{13}$C-NMR for reaction of 1,1'-carbonyldi(imidazole)+4 eq. Acetaldehyde at 80° C. to form 1,1'-(prop-1-ene-1,1-diyl)bis(1H-imidazole).

NMR Characterization of Compounds Prepared $^{1}$H- and $^{13}$C-NMR experiments were collected using a 360 or 500 Hz Bruker Avance NMR Spectrometer, in DMSO-d6, TFA-d, or DCl (in D$_2$O). For all spectra, at least 64 $^{1}$H-NMR scans or at least 15000 $^{13}$C-NMR scans were obtained. 2D Spectra, HSQC or HMBC experiments, were employed on the same instrumentation to support these assignments and correlations. Select representative spectra are provided in FIGS. 1-14.

IR Characterization

Figure 15:
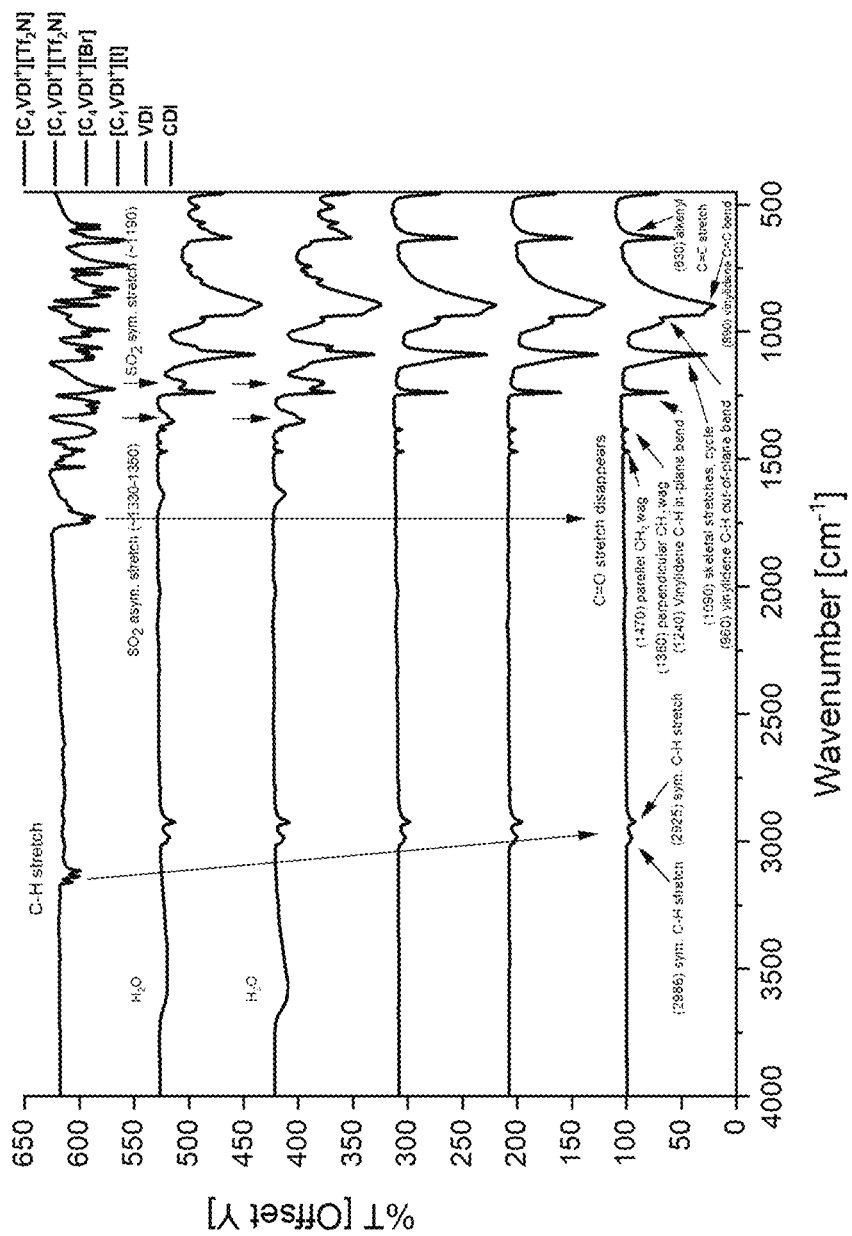
FIG. 15 is FTIR spectra for 1,1'-(ethene-1,1-diyl)bis(1H-imidazole) and corresponding charged products, alongside 1,1'-carbonyldi(imidazole) (as a reference).
Figure 16:
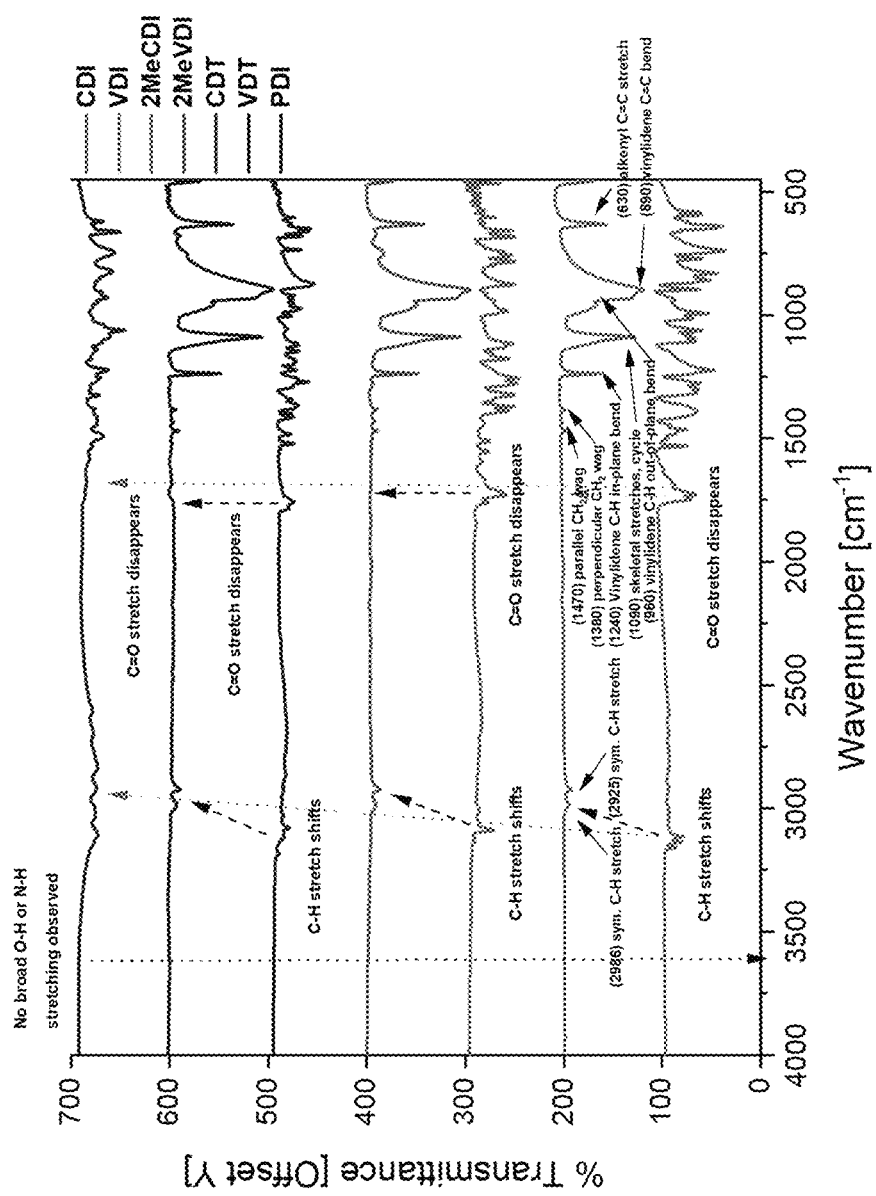
FIG. 16 is FTIR spectra for 1,1'-(ethene-1,1-diyl)bis(1H-imidazole) derivatives (Scheme 1), compared with corresponding carbonyl-precursors.
Figure 17:
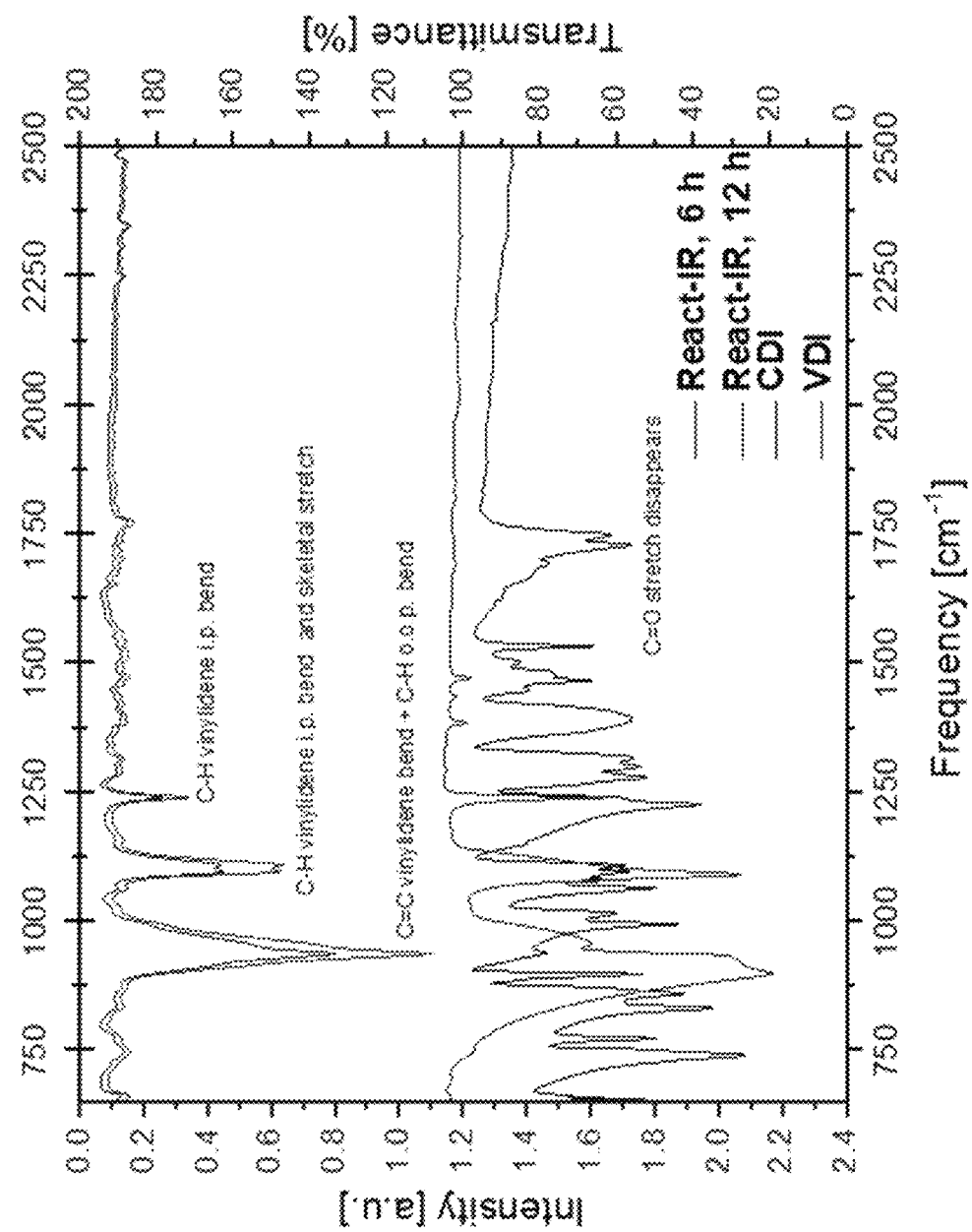
FIG. 17 is in situ FTIR spectra for 1,1'-carbonyldi(imidazole) to 1,1'-(ethene-1,1-diyl)bis(1H-imidazole) transformation.
Figure 18:
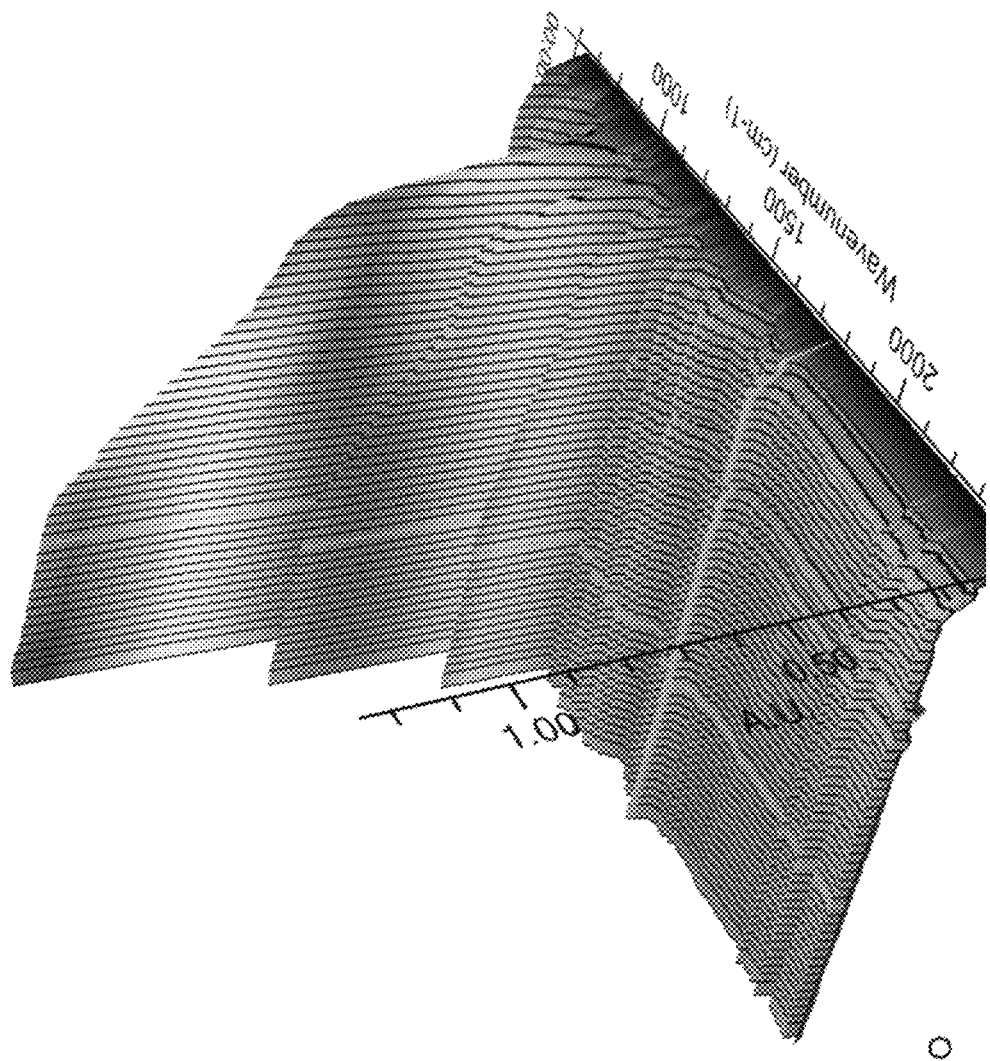
FIG. 18 is n situ FTIR spectra shown over time for 1,1'-carbonyldi(imidazole) to 1,1'-(ethene-1,1-diyl)bis(1H-imidazole) transformation.
Figure 19:
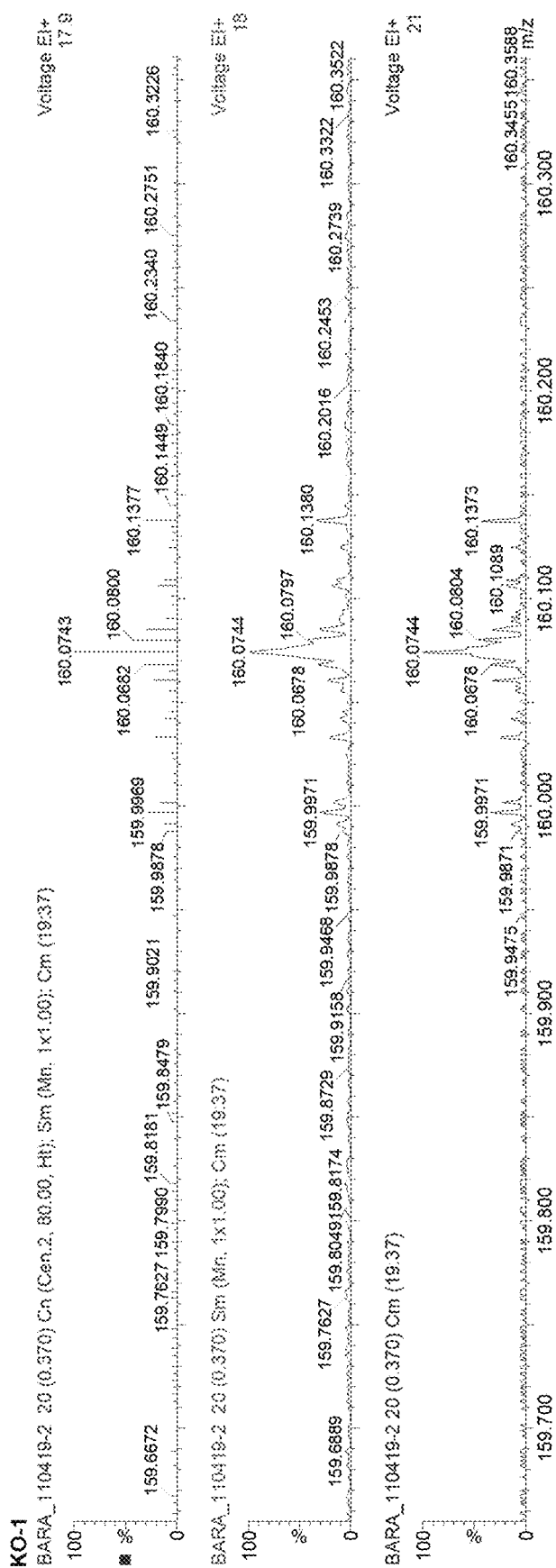
FIG. 19 shows mass spectra for 1,1'-(ethene-1,1-diyl)bis(1H-imidazole).
Figure 20:
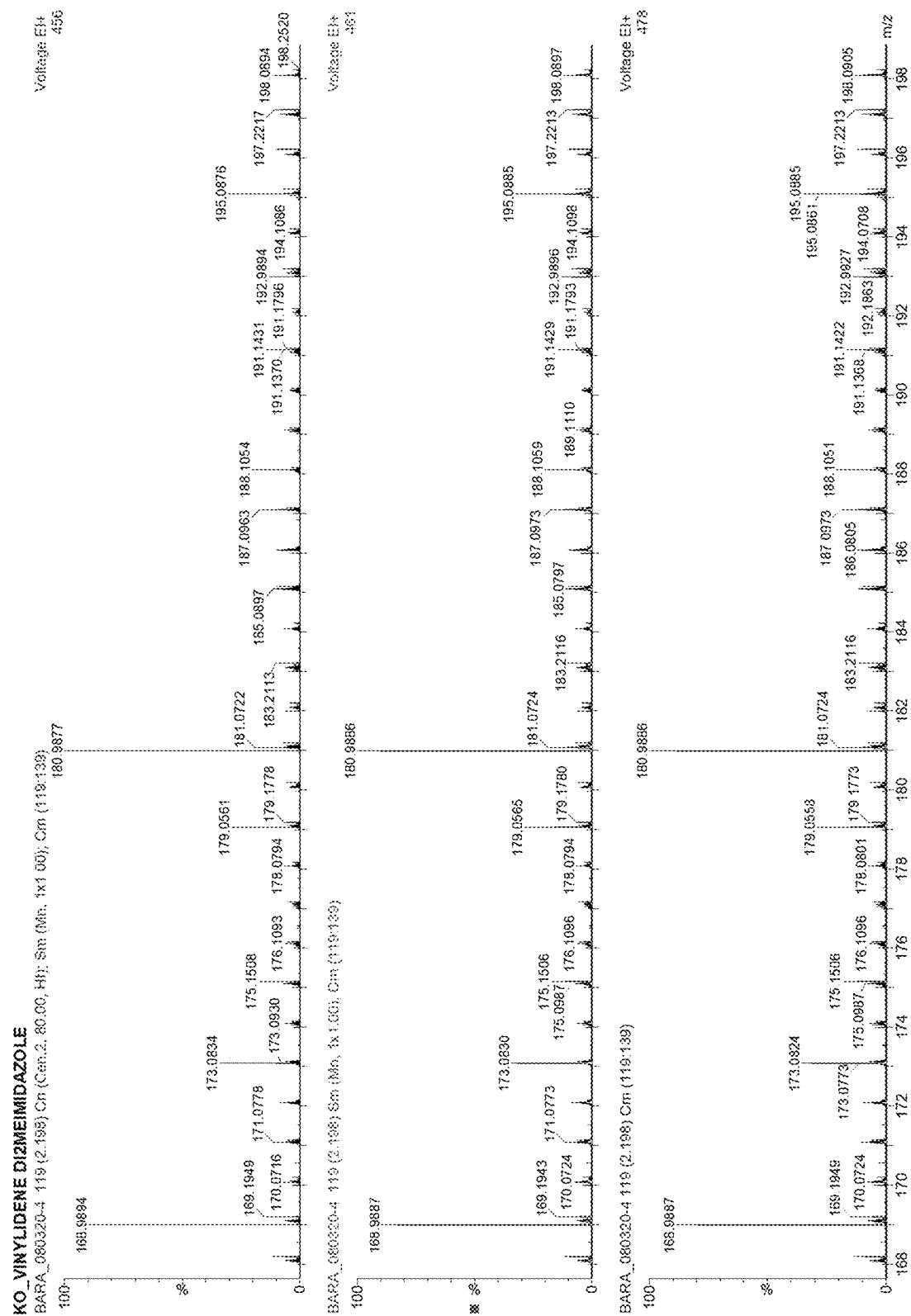
FIG. 20 shows mass spectra for 1,1'-(ethene-1,1-diyl)bis(2-methyl-1H-imidazole).
Figure 21:
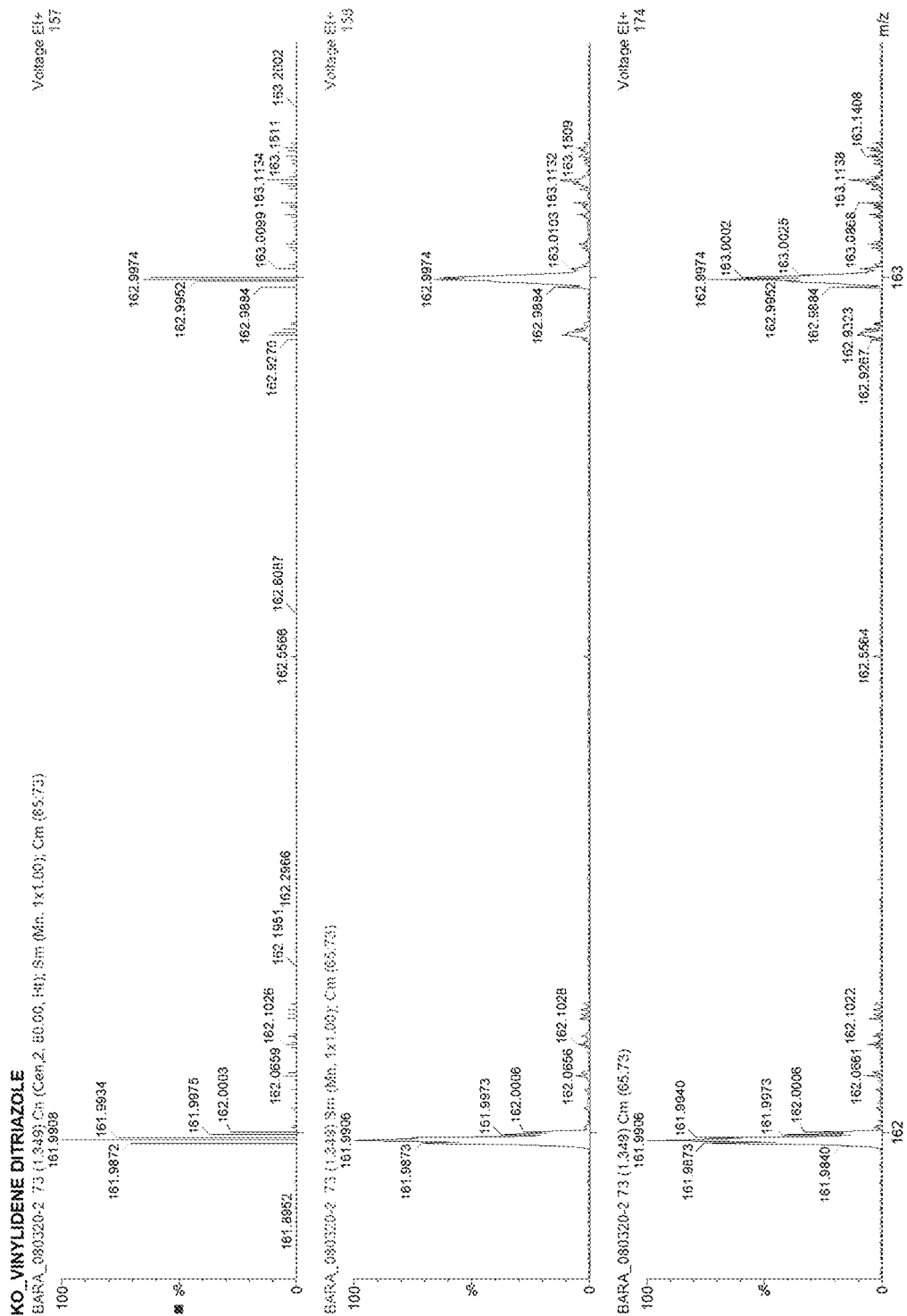
FIG. 21 is shows mass spectra for 1,1'-(ethene-1,1-diyl)bis(1H-1,2,4-triazole).
Figure 22:
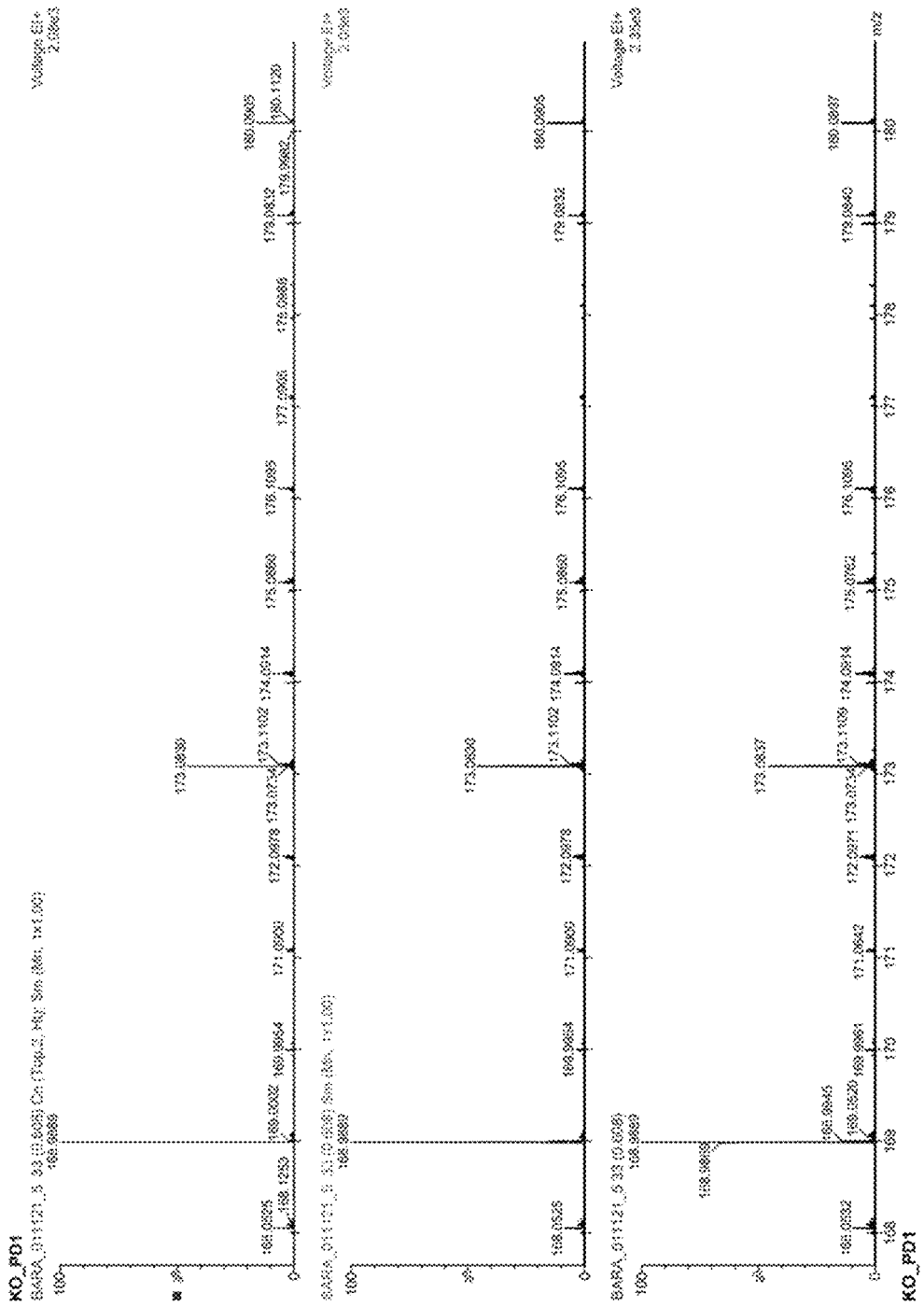
FIG. 22 shows mass spectra for 1,1'-(prop-1-ene-1,1-diyl)bis(1H-imidazole).
Figure 23:
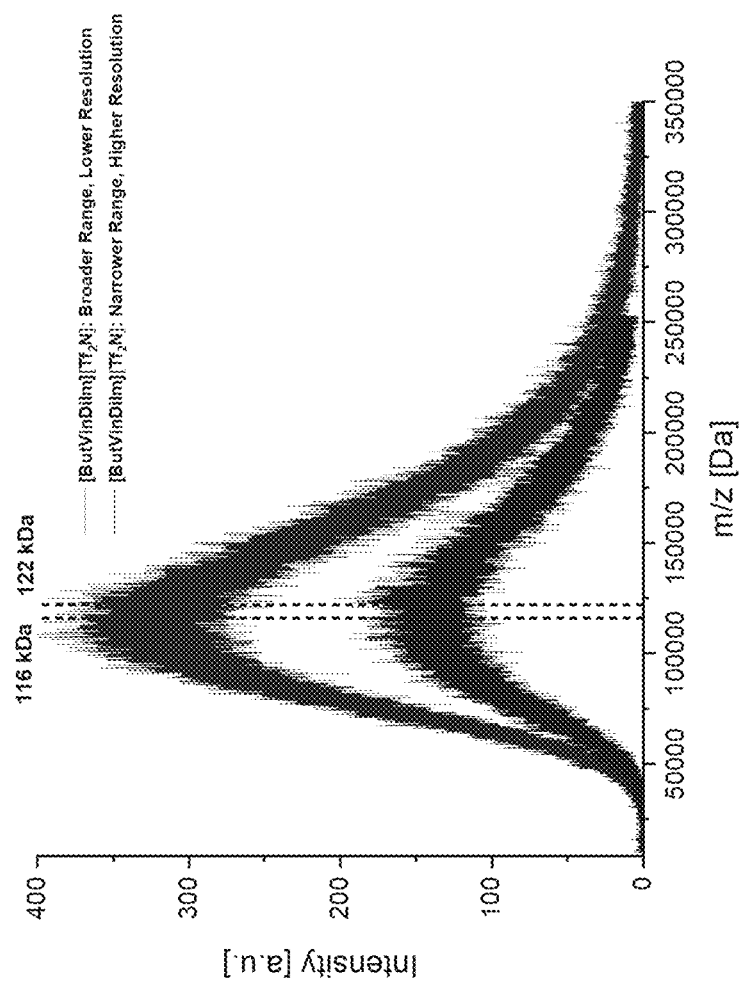
FIG. 23 shows a representative MALDI-TOF spectrum for charged vinylidene-diimidazolium product Polymer 1 with high number average molecular weights.
Figure 24:
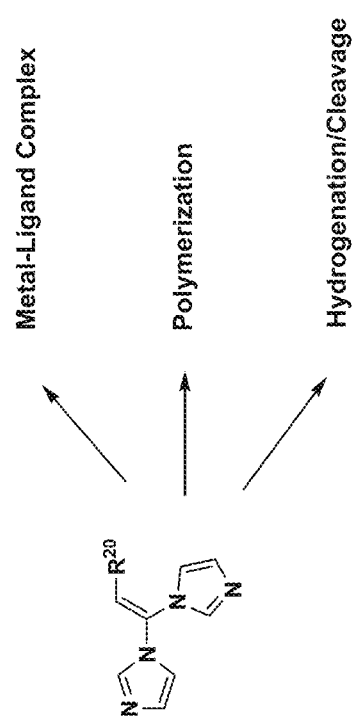
FIG. 24 shows potential transformations of alkene products described herein.

Fourier transform infrared spectroscopy (FT-IR) was performed using a Perkin Elmer ATR-FTIR instrument. In situ FTIR data were collected on a Mettler Toledo ReactIR instrument. Select representative spectra are provided in FIGS. 15-18.

Mass Spectrometry

High Resolution Mass Spectrometry

The exact mass and corresponding formulas for the three vinylidene compounds introduced in this work were confirmed using HRMS. These experiments were performed via solid state electron ionization (EI) techniques utilizing an AutoSpec-Ultima™ NT instrument (Scanning Methods Utilized: Magnetic scan: vary magnetic field, over large mass ranges, nominal accuracy. Voltage scan: vary accelerating voltage, over smaller mass ranges, higher accuracy than magnet scanning; Spectra Analyzed: Magnetic scan centroid mode, Voltage scan centroid mode and elemental analysis, Voltage scan continuum mode, with smoothing, with smoothing and center.)

VinDi(Imid) [Compound I]

Elemental Composition Report | Single Mass Analysis
Tolerance = 5.0 PPM/DBE: min = -1.5, max = 50.0
Isotope cluster parameters: Separation = 1.0 Abundance = 1.0%
Monoisotopic Mass, Odd and Even Electron Ions
93 formula(e) evaluated with 1 result within limits (up to 50 closest results for each mass)
Minimum:                                    -1.5
Maximum:                    4.0       5.0   50.0

| Mass | Calc. Mass | mDa | PPM | DBE | Score | Formula |
|---|---|---|---|---|---|---|
| 160.0744 | 160.0749 | -0.5 | -3.1 | 7.0 | 1 | C8 H8 N4 |

VinDi(2MeImid) [Compound II]

Elemental Composition Report | Single Mass Analysis
Tolerance = 5.0 PPM/DBE: min = -1.5, max = 50.0
Isotope cluster parameters: Separation = 1.0 Abundance = 1.0%
Monoisotopic Mass, Odd and Even Electron Ions
107 formula(e) evaluated with 1 result within limits (up to 50 closest results for each mass)
Minimum:                                    -1.5
Maximum:                    4.0       5.0   50.0

| Mass | Calc. Mass | mDa | PPM | DBE | Score | Formula |
|---|---|---|---|---|---|---|
| 188.1054 | 188.1062 | -0.8 | -4.2 | 7.0 | 1 | C10 H12 N4 |

VinDi(1,2,4-Triazole) [Compound III]

Elemental Composition Report | Single Mass Analysis
Tolerance = 5.0 PPM/DBE: min = -1.5, max = 50.0
Isotope cluster parameters: Separation = 1.0 Abundance = 1.0%
Monoisotopic Mass, Odd and Even Electron Ions
90 formula(e) evaluated with 1 result within limits (up to 50 closest results for each mass)
Minimum:                                    -1.5
Maximum:                    4.0       5.0   50.0

| Mass | Calc. Mass | mDa | PPM | DBE | Score | Formula |
|---|---|---|---|---|---|---|
| 162.0659 | 162.0654 | 0.5 | 3.1 | 7.0 | 1 | C6 H6 N6 |

Propenyl Diimidazole (PDI) [Compound IV]

Elemental Composition Report | Single Mass Analysis
Tolerance = 5.0 PPM/DBE: min = -1.5, max = 50.0
Isotope cluster parameters: Separation = 1.0 Abundance = 1.0%
Monoisotopic Mass, Odd and Even Electron Ions
26 formula(e) evaluated with 1 results within limits (up to 50 closest results for each mass)
Minimum:                                    -1.5
Maximum:                    2.0       5.0   50.0

| Mass | Calc. Mass | mDa | PPM | DBI | Score | Formula |
|---|---|---|---|---|---|---|
| 173.083 | 173.0827 | 0.3 | 1.6 | 7.5 | 1 | C9 H9 N4 |

REFERENCES CITED

All publications mentioned herein are incorporated herein by reference to disclose and describe the methods and/or materials in connection with which the publications are cited.

1. Staudinger, H.; Rathsam, G., Ketene: Über Ketenacetale. XL. Mitteilung. *Helvetica Chimica Acta* 1922, 5 (5), 645-655.
2. McElvain, S. M., The Ketene Acetals. 1949.
3. Akiyama, T.; Itoh, J.; Yokota, K.; Fuchibe, K., Enantioselective Mannich-Type Reaction Catalyzed by a Chiral Brønsted Acid. *Angewandte Chemie International Edition* 2004, 43 (12), 1566-1568.
4. Wenzel, A. G.; Jacobsen, E. N., Asymmetric Catalytic Mannich Reactions Catalyzed by Urea Derivatives: Enantioselective Synthesis of β-Aryl-β-Amino Acids. *Journal of the American Chemical Society* 2002, 124 (44), 12964-12965.
5. Sogah, D. Y.; Hertler, W. R.; Webster, O. W.; Cohen, G. M., Group transfer polymerization—polymerization of acrylic monomers. *Macromolecules* 1987, 20 (7), 1473-1488.
6. Crivello, J. V.; Malik, R.; Lai, Y. L., Ketene acetal monomers: Synthesis and characterization. *Journal of Polymer Science Part A: Polymer Chemistry* 1996, 34 (15), 3091-3102.
7. Jutz, C.; Amschler, J., Über Amidinium-Salze und Ketenaminale. *Chemische Berichte* 1963, 96 (8), 2100-2108.
8. S. M. McElvain, B. E. T., Nitrogen Analogs of The Ketene Acetals. 1945.
9. Weingarten, H.; Wager, J. S., The oxidative coupling reaction of vinylidenebisdialkylamines. *Tetrahedron Letters* 1969, 10 (38), 3267-3268.
10. Yamaguchi, K.; Yabushita, S.; Fueno, T., Zwitterionic mechanisms for photooxygenation reactions of n-activated c-c double bonds: full geometry optimizations of the diradical and zwitterionic intermediates by ab initio SCF method. *Chemical Physics Letters* 1981, 78 (3), 566-571.
11. Shevlin, P. B.; McPherson, D. W.; Melius, P., Reaction of atomic carbon with ammonia. The mechanism of formation of amino acid precursors. *Journal of the American Chemical Society* 1983, 105 (3), 488-491.
12. Gobbi, A.; Frenking, G., Y-Conjugated compounds: the equilibrium geometries and electronic structures of guanidine, guanidinium cation, urea, and 1,1-diaminoethylene. *Journal of the American Chemical Society* 1993, 115 (6), 2362-2372.
13. González, A. I.; Mó, O.; Yáñez, M.; Léon, E.; Tortajada, J.; Morizur, J. P.; Leito, I.; Maria, P. C.; Gal, J. F., Basicity of Acetamidine. Experimental and Theoretical Study. *The Journal of Physical Chemistry* 1996, 100 (24), 10490-10496.
14. Sung, K.; Wu, S.-H.; Wu, R.-R.; Sun, S.-Y., NMR and ab Initio Studies of Amination of Ketenimine: Direct Evidence for a Mechanism Involving a Vinylidenediamine as an Intermediate. *The Journal of Organic Chemistry* 2002, 67 (12), 4298-4303.
15. Kleinpeter, E.; Schulenburg, A., Quantification of the push-pull effect in substituted alkenes. *Tetrahedron Letters* 2005, 46 (36), 5995-5997.
16. Jin, X.; Xiao, M.; Ding, Y.; Zhou, J.; Hu, B., Theoretical Insights on A series of Cyclic Energetic Derivatives. *ChemistrySelect* 2018, 3 (40), 11160-11166.
17. Palaniraja, J.; Roopan, S. M., UV-light induced domino type reactions: synthesis and photophysical properties of unreported nitrogen ring junction quinazolines. *RSC Advances* 2015, 5 (47), 37415-37423.
18. Rickborn, B., The Retro-Diels-Alder Reaction Part II. Dienophiles with One or More Heteroatom. *Organic Reactions* 2004, 223-629.
19. Product class 1: cumulenes. In *Science of Synthesis*, 2007; Vol. 44, pp 9-70.
20. von Angerer, S., Product class 12: pyrimidines. In *Science of Synthesis*, 2004; Vol. 16, pp 379-572.
21. Alk-1-ene-1,1-diamines with retention of the functional group. In *Science of Synthesis*, 2006; Vol. 24, pp 707-746.
22. Product class 3: thioaldehyde and thioketone S,S-dioxides and oxyimides (sulfenes and derivatives). In *Science of Synthesis*, 2004; Vol. 27, pp 123-134.
23. Neidlein, R.; Klotz, U. J., Synthesen, spektroskopische Eigenschaften von Alkylmercaptoalkylaminomethylensulfonamiden und chemisches Reaktionsverhalten von 1,1-Bis-(dimethylamino)-ethylen. *Monatshefte für Chemie/Chemical Monthly* 1985, 116 (5), 651-660.
24. Dove, A. P., Organic Catalysis for Ring-Opening Polymerization. *ACS Macro Letters* 2012, 1 (12), 1409-1412.
25. Kantlehner, W., Product Subclass 17: 1,1-Bis(nitrogen-functionalized) Alk-1-enes: 24.2.17.1 Alk-1-ene-1,1-diamines. *Science of Synthesis* 2006, 24, 571-705.
26. Balasanthiran, V. Chemistry of Bismuth, Chromium and Magnesium Complexes and Their Applications in the Ring-Opening Polymerization of Cyclic Esters and Epoxides. The Ohio State University, 2015.
27. Taylor, J. E.; Bull, S. D.; Williams, J. M. J., Amidines, isothioureas, and guanidines as nucleophilic catalysts. *Chemical Society Reviews* 2012, 41 (6), 2109-2121.
28. Trost, B. M.; McClory, A., Metal Vinylidenes as Catalytic Species in Organic Reactions. *Chemistry—An Asian Journal* 2008, 3 (2), 164-194.
29. Xiong, Y.; Zhang, X.; Huang, T.; Cao, S., Synthesis of N-(alpha-fluorovinyl)azoles by the reaction of difluoroalkenes with azoles. *J Org Chem* 2014, 79 (14), 6395-402.
30. Zhang, C.; Shi, Y.-L.; Zhang, L.-Y.; Yuan, D.-P.; Ban, M.-T.; Zheng, J.-Y.; Liu, D.-H.; Guo, S.-N.; Cui, D.-M., NaOH-promoted reaction of 1,1-dihaloalkenes and 1H-azoles: synthesis of dihetaryl substituted alkenes. *New Journal of Chemistry* 2018, 42 (21), 17732-17739.
31. Naumann, S., Synthesis, properties & applications of N-heterocyclic olefins in catalysis. *Chemical Communications* 2019, 55 (78), 11658-11670.
32. Roy, M. M. D.; Rivard, E., Pushing Chemical Boundaries with N-Heterocyclic Olefins (NHOs): From Catalysis to Main Group Element Chemistry. *Accounts of Chemical Research* 2017, 50 (8), 2017-2025.
33. Ogata, M.; Matsumoto, H.; Kida, S.; Shimizu, S., Reaction of N,N'-carbonyldiimidazole and N,N'-thionyldiimidazole with carbonyl compounds: a new imidazole transfer reaction. *Tetrahedron Letters* 1979, 20 (52), 5011-5014.
34. Kamlesh J. Padiya, †Sandip Gavade, ‡ Bhavana Kardile, †Manojkumar Tiwari, ‡ Swapnil Bajare, † Madhav Mane, ‡ Vivek Gaware,‡ Shaji Varghese,‡ Dipak Harel,‡ and Suresh Kurhade, Unprecedented "In Water" Imidazole Carbonylation: Paradigm Shift for Preparation of Urea and Carbamate. *Organic Letters* 2012, 14 (11), 2814-2817.
35. Nugent, J.; Campbell, S. G.; Vo, Y.; Schwartz, B. D., Solvent-Free Synthesis of Cyanoformamides from Carbamoyl Imidazoles. *European Journal of Organic Chemistry* 2017, 2017 (34), 5110-5118.

36. Ballesteros, P.; Elguero, J.; Claramunt, R. M., Reactivity of azoles towards benzaldehyde and its dimethylacetal. Synthesis of N,N'-diazolylphenylmethanes. *Tetrahedron* 1985, 41 (24), 5955-5963.
37. Paul, R.; Anderson, G. W., N,N'-Carbonyldiimidazole, a New Peptide Forming Reagent1. *Journal of the American Chemical Society* 1960, 82 (17), 4596-4600.
38. Mote, S. P.; Deshmukh, S. P., SYNTHESIS AND ANTI-MICROBIAL ACTIVITY OF NOVEL ACETYLATED MALTOSYL CARBAMIDES, BENZOTHIAZOLYL CARBAMIDES AND CARBAMATES. *Rasayan Journal of Chemistry* 2011, 4 (1), 29-35.
39. Parmar, S. S.; Dwivedi, C.; Ali, B., Substituted carbamides: Interrelationship between anticonvulsant activity and inhibition of nicotinamide adenine dinucleotide-dependent pyruvic acid oxidation. *Journal of Pharmaceutical Sciences* 1972, 61 (9), 1366-1369.
40. Kishore, V.; Kumar, S.; Parmar, S. S.; Stenberg, V. I., Anti-Inflammatory and Antiproteolytic Properties of 1-(1-Naphthylacetyl)-3-substituted Carbamides. *Journal of Pharmaceutical Sciences* 1976, 65 (7), 1078-1081.
41. Roberto Di Santo; Tafi, A.; Costi, R.; Botta, M.; Artico, M.; Corelli, F.; Forte, M.; Caporuscio, F.; Angiolella, L.; Palamara, A. T., Antifungal Agents. 11. N-Substituted Derivatives of 1-[(Aryl)(4-aryl-1H-pyrrol-3-yl)methyl]-1H-imidazole: Synthesis, Anti-*Candida* Activity, and QSAR Studies. *Journal of Medicinal Chemistry* 2005, 48, 5140-5153.
42. Kizhnyaev, V. N.; Krakhotkina, E. A.; Petrova, T. L.; Kazantseva, M. V.; Pokatilov, F. A.; Verkhozina, O. N., Synthesis and properties of azole-containing ionenes. *Polymer Science Series B* 2011, 53 (3-4), 144-150.
43. Critchley, J. P., A review of the poly(azoles). *Progress in Polymer Science* 1970, 2, 47-161.
44. O'Harra, K. E.; Bara, J. E., Toward controlled functional sequencing and hierarchical structuring in imidazolium ionenes. *Polymer International* 2020.
45. Anderson, E. B.; Long, T. E., Imidazole- and imidazolium-containing polymers for biology and material science applications. *Polymer* 2010, 51 (12), 2447-2454.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A method for synthesizing a compound of Formula VI

the method comprising reacting a compound of Formula II

with a compound of Formula VII

or an acetal derivative or a polyacetal derivative thereof, at elevated temperature to form the compound of Formula VI; wherein:

$R^1$ is selected from hydrogen, alkyl, cycloalkyl, heterocycle, aryl, heteroaryl, $OR^3$, $SR^3$, and $NR^4R^5$, each of which may be optionally substituted with one or more Z groups;

$R^2$ is $NR^6R^7$;

$R^3$ is selected from alkyl, cycloalkyl, heterocycle, aryl, and heteroaryl, each of which may be optionally substituted with one or more Z groups;

$R^4$ and $R^5$ are independently selected from hydrogen, alkyl, cycloalkyl, heterocycle, aryl, and heteroaryl, each of which may be optionally substituted with one or more Z groups; or $R^4$ and $R^5$ may be brought together with the nitrogen to which they are attached to form a heterocycle ring or a heteroaryl ring, wherein said heterocycle ring or heteroaryl ring may be optionally substituted with one or more Z groups;

$R^6$ and $R^7$ are independently selected hydrogen, alkyl, cycloalkyl, heterocycle, aryl, and heteroaryl, each of which may be optionally substituted with one or more Z groups; or $R^6$ and $R^7$ may be brought together with the nitrogen to which they are attached to form a heterocycle ring or a heteroaryl ring, wherein said heterocycle ring or heteroaryl ring may be optionally substituted with one or more Z groups;

R[20] is selected from hydrogen, alkyl, cycloalkyl, heterocycle, aryl, and heteroaryl, each of which may be optionally substituted with one or more Z groups; and Z is independently selected at each occurrence from alkyl, haloalkyl, alkoxy, alkenyl, alkynyl, aryl, heteroaryl, cycloalkyl, heterocycle, aldehyde, amino, carboxylic acid, ester, ether, halo, hydroxy, keto, nitro, cyano, azido, silyl, sulfo-oxo, sulfonyl, sulfone, sulfoxide, sulfonylamino, and thiol.

2. The method of claim 1, wherein the compound of Formula VII, or acetal derivative or polyacetal derivative thereof, is paraformaldehyde.

3. The method of claim 1, wherein the compound of Formula VII, or acetal derivative or polyacetal derivative thereof, is dimethoxymethane.

4. The method of claim 1, wherein the compound of Formula VII, or acetal derivative or polyacetal derivative thereof, is 1,3,5-trioxane.

5. The method of claim 1, wherein the compound of Formula VII, or acetal derivative or polyacetal derivative thereof, is acetaldehyde.

6. The method of claim 1, wherein the molar ratio of the compound of Formula VII, or acetal derivative or polyacetal derivative thereof, to the compound of Formula II is about 2:1, about 2.5:1, about 3:1, about 3.5:1, or about 4:1.

7. The method of claim 1, wherein the compound of Formula II is reacted with the compound of Formula VII, or acetal derivative or polyacetal derivative thereof, at a temperature from about 50° C. to about 120° C.

8. The method of claim 1, wherein the compound of Formula II is reacted with the compound of Formula VII, or acetal derivative or polyacetal derivative thereof, in the presence of a solvent.

9. The method of claim 8, wherein the solvent is selected from pentane, cyclopentane, hexane, cyclohexane, benzene, carbon tetrachloride, toluene, 1,4-dioxane, diethyl ether, chloroform, dichloromethane, tetrahydrofuran, ethyl acetate, acetone, dimethylformamide, acetonitrile, dimethylsulfoxide, nitromethane, propylene carbonate, formic acid, n-butanol, isopropyl alcohol, n-propanol, ethanol, methanol, acetic acid, and water, or combinations thereof.

10. The method of claim 1, wherein R[1] is NR[4]R[5].

11. The method of claim 10, wherein R[4] and R[5] are brought together with the nitrogen to which they are attached to form a heterocycle ring or a heteroaryl ring, each of which is optionally substituted with one or more Z groups.

12. The method of claim 1, wherein R[1] is selected from

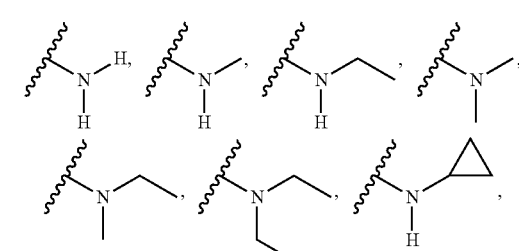

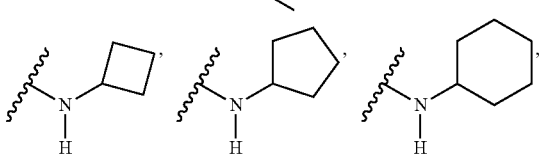

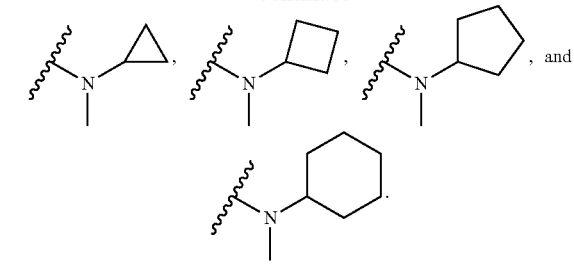

13. The method of claim 1, wherein R[1] is selected from

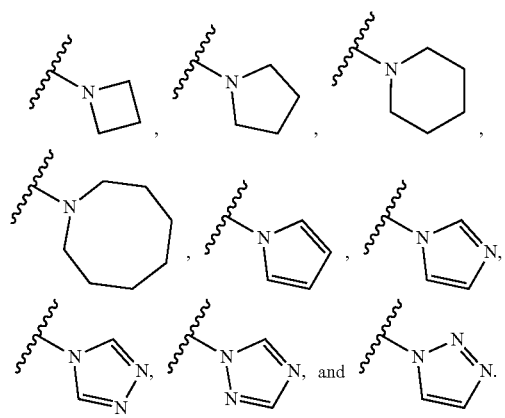

14. The method of claim 1, wherein R[6] and R[7] are brought together with the nitrogen to which they are attached to form a heterocycle ring or a heteroaryl ring, each of which is optionally substituted with one or more Z groups.

15. The method of claim 1, wherein R[2] is selected from

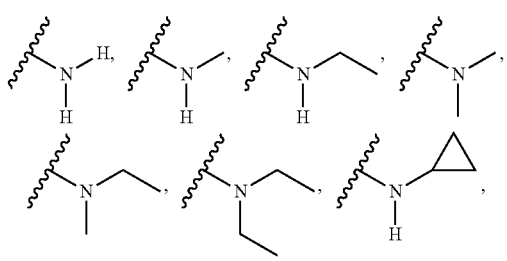

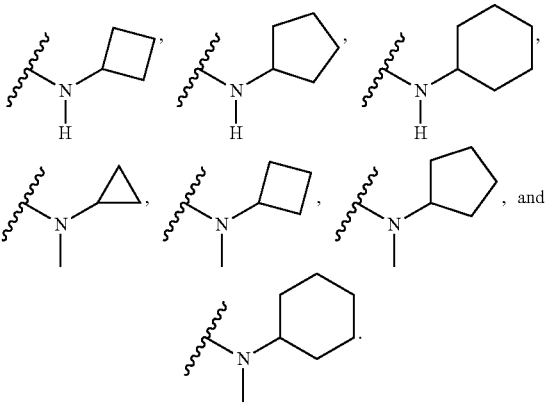

16. The method of claim 1, wherein $R^2$ is selected from

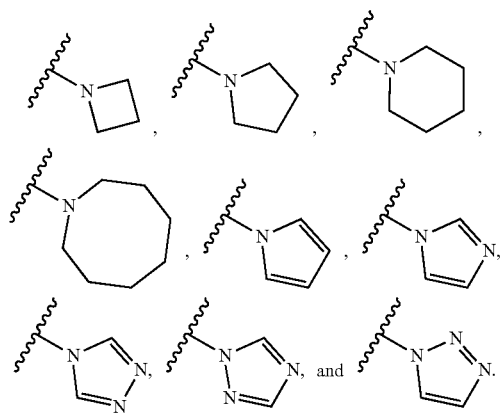

17. The method of claim 1 wherein the compound of Formula VI is selected from:

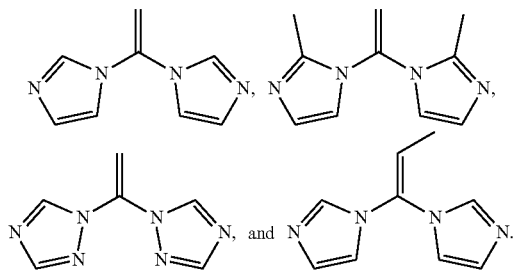

18. A compound of Formula I-a or Formula VI-a:

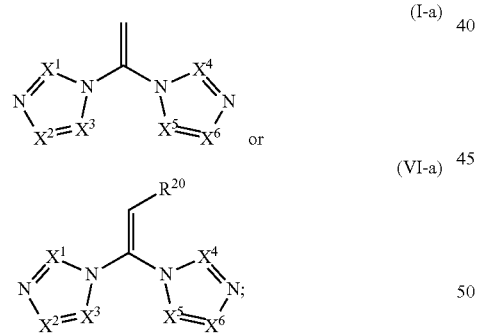

wherein:
$X^1$, $X^2$, $X^3$, $X^4$, $X^5$, and $X^6$ are each selected from N, CH, or C—Z,
wherein at least one of $X^1$, $X^2$, $X^3$, $X^4$, $X^5$, and $X^6$ is C—Z,
wherein no more than one of $X^1$, $X^2$, and $X^3$ is N;
wherein no more than one of $X^4$, $X^5$, and $X^6$ is N;
$R^{20}$ is selected from hydrogen, alkyl, cycloalkyl, heterocycle, aryl and heteroaryl, each of which may be optionally substituted with one or more Z groups; and
Z is independently selected at each occurrence from alkyl, haloalkyl, alkoxy, alkenyl, alkynyl, aryl, heteroaryl, cycloalkyl, heterocycle, aldehyde, amino, carboxylic acid, ester, ether, halo, hydroxy, keto, nitro, cyano, azido, silyl, sulfo-oxo, sulfonyl, sulfone, sulfoxide, sulfonylamino, and thiol.

19. A compound of Formula III or Formula III-a

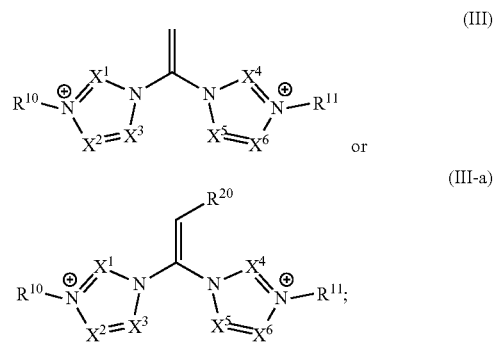

and one or more anions balancing the charge of the compound of Formula III or Formula III-a;
wherein:
$R^{10}$ and $R^{11}$ are independently selected from alkyl, cycloalkyl, aryl, or heteroaryl, each of which may be optionally substituted with one or more Z groups;
$X^1$, $X^2$, $X^3$, $X^4$, $X^5$ and $X^6$ are independently selected from N, C—H, or C—Z;
wherein no more than one of $X^1$, $X^2$, and $X^3$ are N;
wherein no more than one of $X^4$, $X^5$, and $X^6$ are N;
$R^{20}$ is selected from hydrogen, alkyl, cycloalkyl, heterocycle, aryl, and heteroaryl, each of which may be optionally substituted with one or more Z groups; and
Z is independently selected at each occurrence from alkyl, haloalkyl, alkoxy, alkenyl, alkynyl, aryl, heteroaryl, cycloalkyl, heterocycle, aldehyde, amino, carboxylic acid, ester, ether, halo, hydroxy, keto, nitro, cyano, azido, silyl, sulfo-oxo, sulfonyl, sulfone, sulfoxide, sulfonylamino, and thiol.

20. The compound of claim 19 selected from:

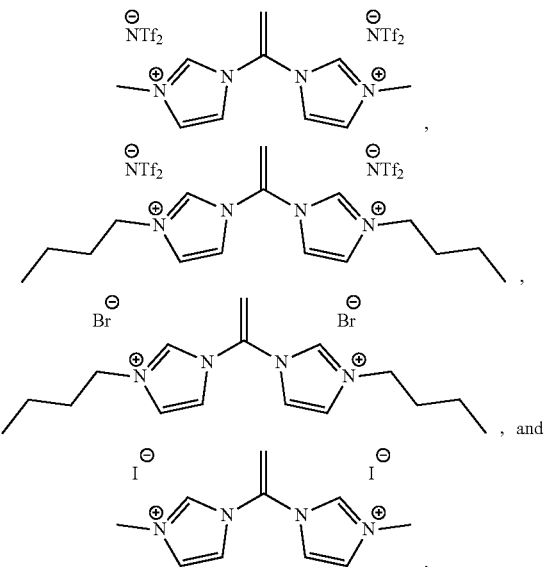

* * * * *

UNITED STATES PATENT AND TRADEMARK OFFICE
CERTIFICATE OF CORRECTION

PATENT NO. : 11,572,355 B2
APPLICATION NO. : 17/322332
DATED : February 7, 2023
INVENTOR(S) : Jason Edward Bara et al.

It is certified that error appears in the above-identified patent and that said Letters Patent is hereby corrected as shown below:

In the Specification

In Column 17, Lines 52-66, delete:

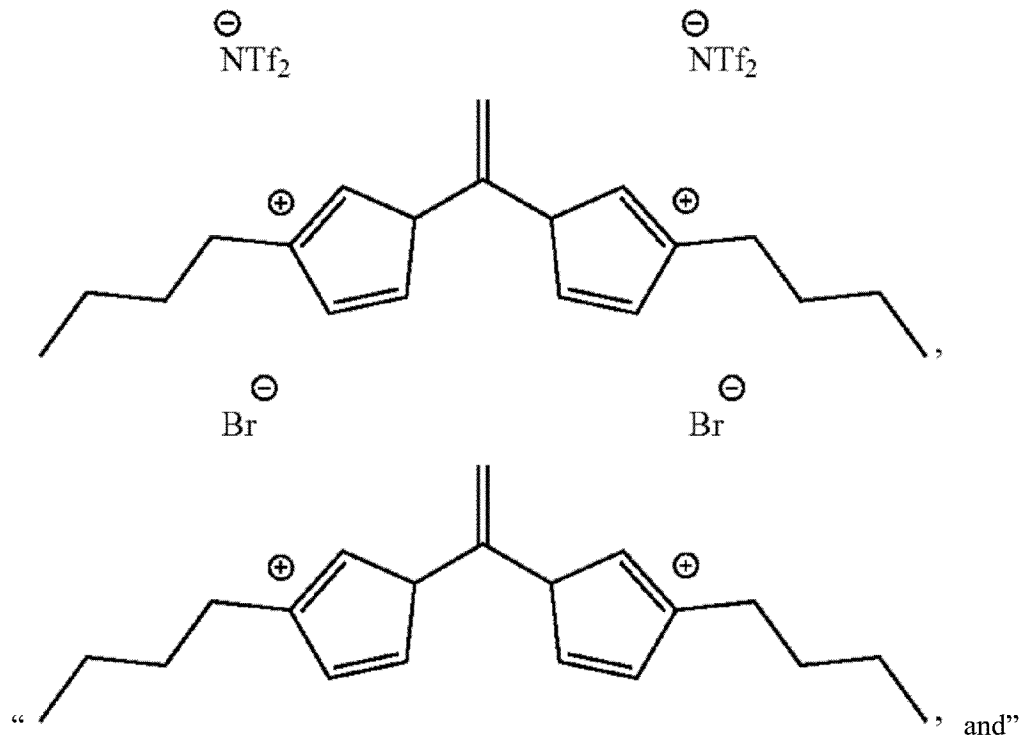

" , and"

Signed and Sealed this
Thirty-first Day of October, 2023

Katherine Kelly Vidal
*Director of the United States Patent and Trademark Office*

And insert:
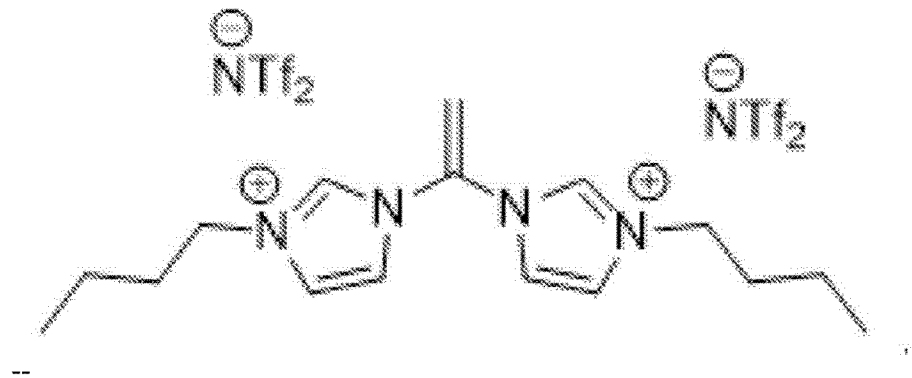
--                                                                                                              ,
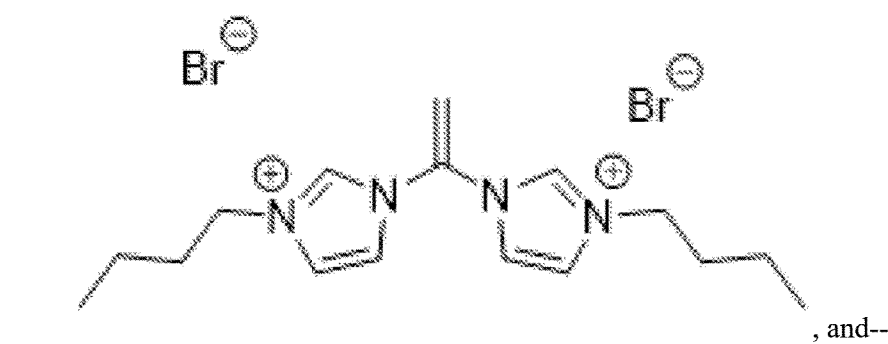
                                                                                                         , and--